United States Patent
Saxell et al.

(10) Patent No.: US 8,188,136 B2
(45) Date of Patent: May 29, 2012

(54) CRYSTALLINE MODIFICATION OF FIPRONIL

(75) Inventors: Heidi Emilia Saxell, Carlsberg (DE); Peter Erk, Frankenthal (DE); Claude Taranta, Stutensee (DE); Thomas Kröhl, Schriesheim (DE); Gerhard Cox, Bad Dürkheim (DE); Martin Sukopp, Mannheim (DE); Gautam R. Desiraju, Hyderabad (IN); Rahul Banerjee, Pune (IN); Prashant M. Bhatt, Stellenbosch (ZA)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/513,915

(22) PCT Filed: Nov. 5, 2007

(86) PCT No.: PCT/EP2007/061897
§ 371 (c)(1),
(2), (4) Date: Nov. 2, 2009

(87) PCT Pub. No.: WO2008/055883
PCT Pub. Date: May 15, 2008

(65) Prior Publication Data
US 2010/0041727 A1    Feb. 18, 2010

(30) Foreign Application Priority Data
Nov. 10, 2006  (EP) ..................................... 06023436

(51) Int. Cl.
*A01N 43/56* (2006.01)
*C07D 231/38* (2006.01)
(52) U.S. Cl. ..................................... 514/407; 548/367.4
(58) Field of Classification Search ........................ None
See application file for complete search history.

(56) References Cited

U.S. PATENT DOCUMENTS

| | | | |
|---|---|---|---|
| 5,283,337 A | 2/1994 | Wakselman et al. | |
| 5,618,945 A | 4/1997 | Casado et al. | |
| 5,631,381 A | 5/1997 | Huang et al. | |
| 6,346,542 B1 | 2/2002 | Huber | |
| 8,063,092 B2 * | 11/2011 | Saxell et al. | 514/407 |

FOREIGN PATENT DOCUMENTS

| | | |
|---|---|---|
| CN | 1 374 298 | 10/2002 |
| EP | 0 295 117 | 12/1988 |
| EP | 0 374 061 | 6/1990 |
| EP | 0 460 940 | 12/1991 |
| EP | 0 484 165 | 5/1992 |
| EP | 0 668 269 | 8/1995 |
| EP | 0 967 206 | 12/1999 |
| EP | 1 331 222 | 7/2003 |
| WO | WO 00/62616 | 10/2000 |
| WO | WO 01/30760 | 5/2001 |
| WO | WO 2007/069254 | 6/2007 |
| WO | WO 2008/055881 | 5/2008 |
| WO | WO 2008/055882 | 5/2008 |
| WO | WO 2008/055884 | 5/2008 |

OTHER PUBLICATIONS

Huilong, Yang et al., "Study on the Synthesis of Regent", Journal of Hebei University of Science and Technology, 2004, p. 69-73, vol. 25, No. 2.
Pesticide Manual, 13th Ed. (2003), The British Crop Protection Council Long, Alton, Hampshire, UK, pp. 433-435.
Tang, Ri-Yuan, et al., "5-Amino-1-[2,6-dichloro-4-(trifluoromethyl)-phenyl]-4-(trifluoromethylsulfanyl)-iH-pyrazole-3-carbonitrile", Acta Crystallographica Section E, Structure reports Online, 2005, p. 04374-04375, vol. E61, No. 12.
International Search Report an Written Opinion of the ISA, completed Jan. 23, 2008, in International Application No. PCT/EP2007/061897, filed Nov. 5, 2007.
International Preliminary Report on Patentability dated Feb. 2, 2009, from corresponding International Application No. PCT/EP2007/061897, filed Nov. 5, 2007.
http://wwww.fao.org/ag/AGP/AGPP/Pesticid/Specs/docs/Pdf/old/FIPR98.pdf.
Third Party Submission against corresponding European Patent Application No. 07 822 226.2, dated Aug. 19, 2009.
Third Party Submission against corresponding European Patent Application No. 07 822 226.2, dated Oct. 27, 2010.
U.N. Food and Agriculture Organization specification on Fipronil, dated 1998 http://wwww.fao.org/ag/AGP/AGPP/Pesticid/Specs/docs/Pdf/old/FIPR98.pdf.
Brittain, et al. #2 "Effects of pharmaceutical processing on drug polymorphs and solvates" in Polymorphism in Pharmaceutical Solids, vol. 95, p. 331-361, 2000.
Express-Pharma-Online, "Polymorphism of Pharmaceuticals: Challenges and Opportunities", (http://www.expresspharmaonline.com/20031023/edit02.shtml) 2003.
Office Action for U.S. Appl. No. 12/514,082, dated Feb. 17, 2011.
Office Action (Final) for U.S. Appl. No. 12/513,904 dated Apr. 28, 2011.
Office Action for U.S. Appl. No. 12/513,904 dated Dec. 6, 2010.
Office Action for U.S. Appl. No. 12/513,087, dated Apr. 5, 2011.

* cited by examiner

*Primary Examiner* — Sun Jae Loewe
(74) *Attorney, Agent, or Firm* — Brinks Hofer Gilson & Lione

(57) ABSTRACT

The present invention relates to a crystalline modification of fipronil, to process for the preparation of the same, to pesticidal and parasiticidal mixtures and compositions comprising said crystalline modification and to their use for combating pests and parasites.

6 Claims, 3 Drawing Sheets

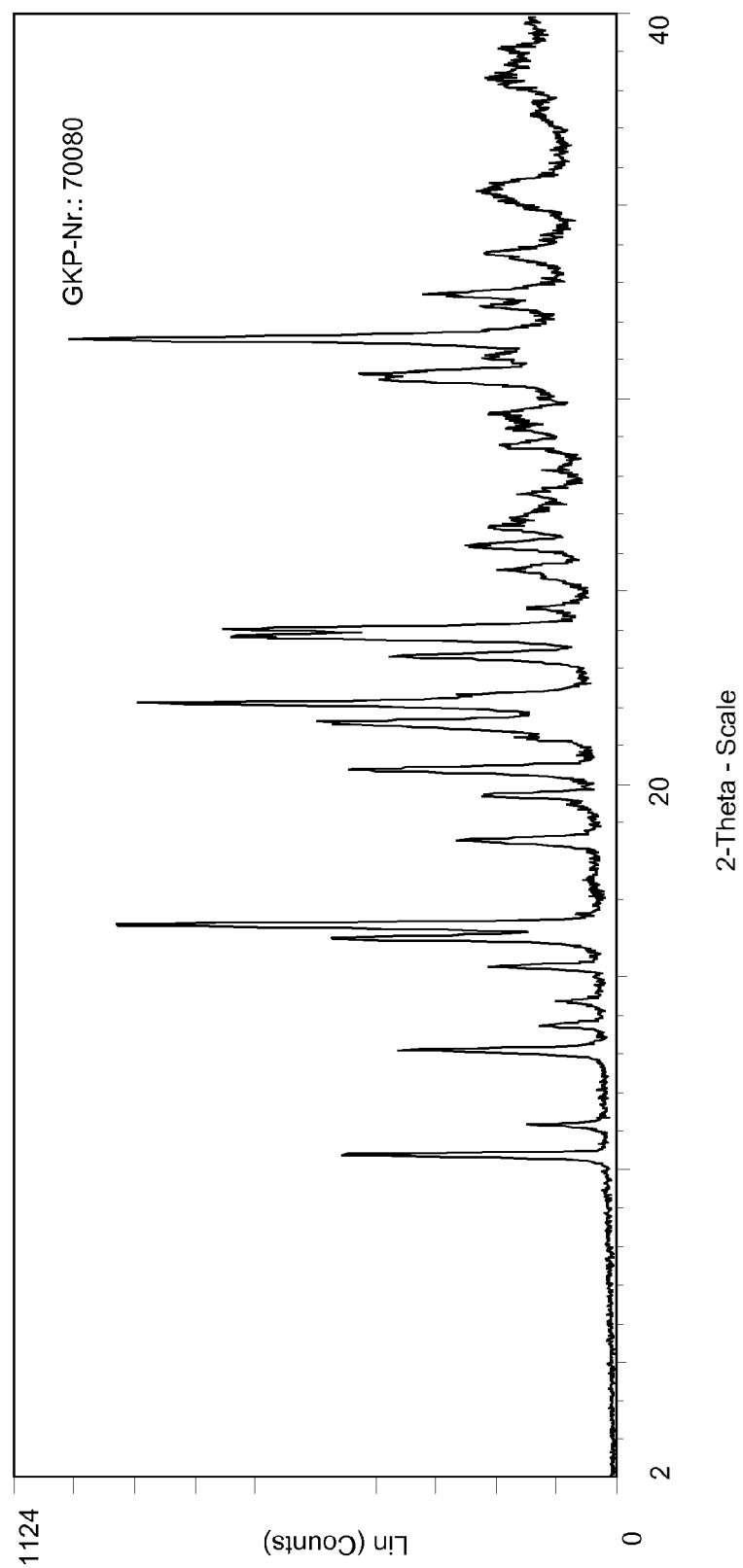
Figure 1. Powder diffractogram

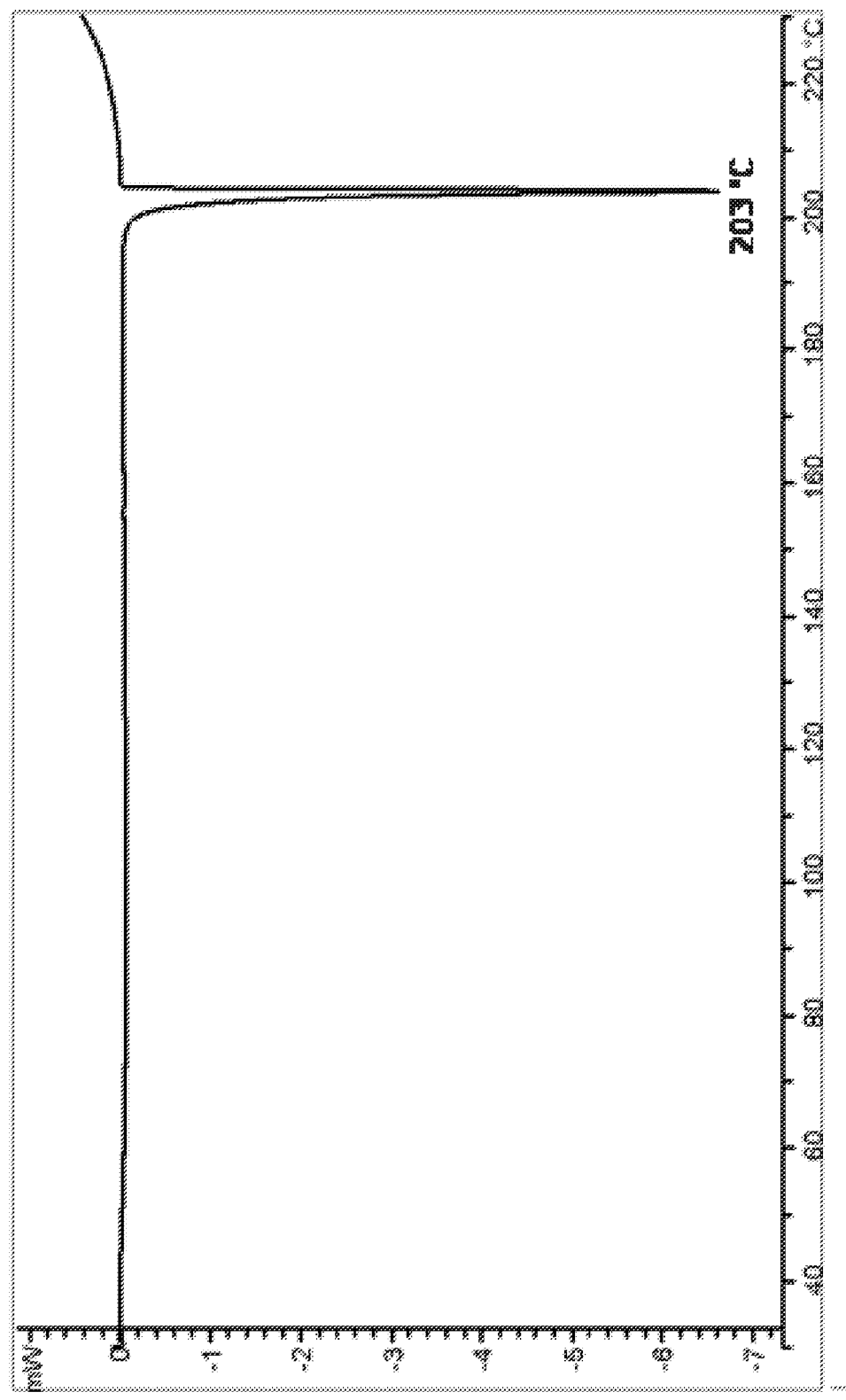
Figure 2. Differential Scanning Calorimetry Thermogram

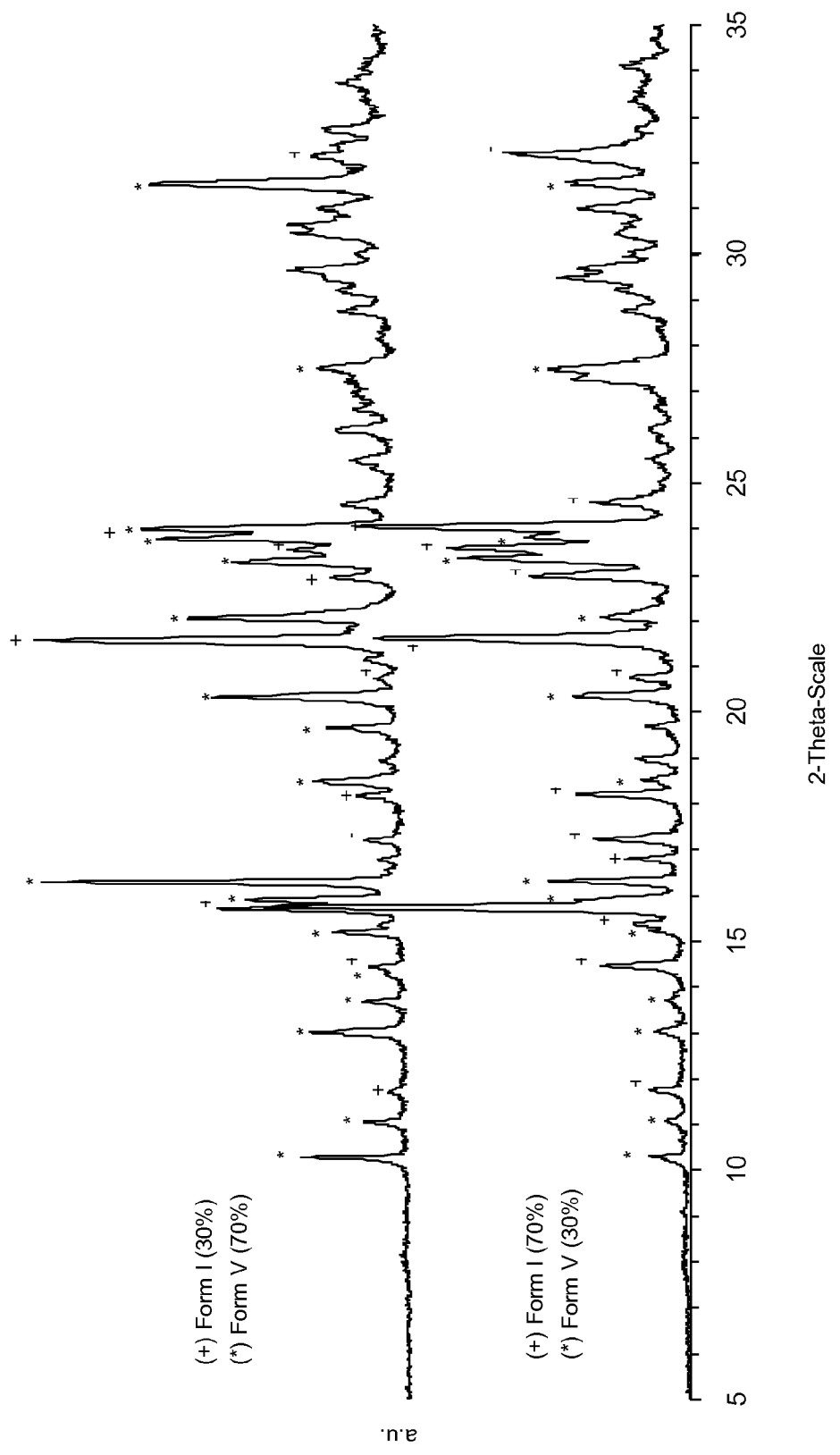
Figure 3: X-ray powder diffractograms of mixtures of modifications I and V

CRYSTALLINE MODIFICATION OF FIPRONIL

This application is a National Stage application of International Application No. PCT/EP2007/061897, filed Nov. 5, 2007, the entire contents of which is hereby incorporated herein by reference. This application also claims the benefit under 35 U.S.C. §119 of European Patent Application No. 06023436.6, filed Nov. 10, 2006, the entire contents of which is hereby incorporated herein by reference.

The present invention relates to a novel crystalline modification of fipronil, to a process for the preparation of the same, to pesticidal and parasiticidal mixtures and compositions comprising said crystalline modification and to their use for combating pests and parasites.

Fipronil (formula I) is an active compound for controlling certain insect and acarid pests, and parasites.

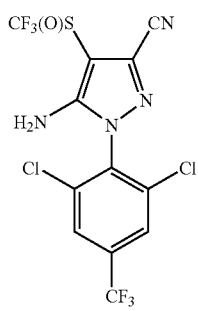

I

Various processes for the preparation of fipronil have been described, generally and in detail. Documents which give detailed preparation procedures are e.g. EP 295 117; EP 460 940; EP 484 165; EP 668 269; EP 967 206; EP 1 331 222; EP 0 374 061; U.S. Pat. No. 5,631,381; CN 1374298; or J. of Heibei University of Science and Technology, Vol. 25 (2), Sum 69 (2004), Dok. Serial No. 1008-1542 (2004) 02-0018-03.

Characterization of the fipronil material obtained by the processes described in the prior art is usually done by $^1$H-NMR analysis and/or measurement of the melting point. The described melting points are in the range of from 187° C. to 203° C., mostly in the range of from 195° C. to 203° C. In the Pesticidal Manual, 13$^{th}$ Edition (2003), British Crop Protection Council, p. 433, fipronil is described as a white solid with a melting point of 200 to 201° C., with technical fipronil having a melting point of 195.5° C. to 203° C. Observations of different crystalline forms of fipronil have not been described, let alone any characterization of a certain crystalline modification or a preparation procedure for obtaining a certain crystalline modification.

For the large-scale preparation and formulation of a market compound such as fipronil, it is of crucial importance to know whether different crystalline modifications (also frequently referred to as polymorphs) of a compound exist, how they can be obtained, and what their characteristic properties are. Crystalline modifications of one compound may have very different properties, for example with regard to solubility, rate of dissolution, suspension stability, stability during grinding, vapour pressure, optical and mechanical properties, hygroscopicity, crystal size, filtration properties, desiccation, density, melting point, degradation stability, stability against phase transformation into other crystalline modifications, colour, and even chemical reactivity.

For example, different crystalline modifications frequently manifest themselves in different forms of the crystals, such as needles or plates. This is of relevance for e.g. a filtration step in the preparation procedure. Plates typically will clog the pores of a filter leading to loss of time and product and tedious and expansive cleaning work. Also, a crystalline modification being present as plates and a crystalline modification being present as needles can have significantly different bulk densities which has implications for storage and packaging. Another relevant aspect, especially in the production of pesticides, is whether the crystalline modification is present as a fine powder which can produce hazardous dusts, or as dust-free larger crystals.

Against this background, it has been an object of the present invention to find and characterize a novel crystalline modification of fipronil.

A further object has been to find preparation procedures for the novel crystalline modification which reproducibly give the crystalline modification.

Another object of the invention has been to find preparation procedures which give the novel crystalline modification V in high yield.

Yet another object of the invention has been to find preparation procedures which give the novel crystalline modification essentially excluding other crystalline modification forms (i.e. in over 80% by weight). This ensures reproducibility and stability in all aspects of the production, transportation, storage and use of the corresponding solid state form.

Accordingly, a novel crystalline modification of fipronil, a process for its preparation, pesticidal and parasiticidal mixtures and compositions comprising it and its use for combating pests and parasites has been found. The novel crystalline modification of fipronil is defined as "novel crystalline modification V" throughout this application.

Also, most surprisingly, 3 other crystalline modifications of fipronil have been found, which are subject to co-pending patent applications. Especially surprising was that the present crystalline modification V of fipronil has a very similar melting point as a second crystalline modification I, both melting points lying in the range of the melting points given in the prior art (i.e. 195 to 203° C.). Moreover, two further crystalline modifications II and IV of fipronil, as described in co-pending applications, undergo phase transformations during heating into the more stable forms I and V, and thus in a typical melting point measurement will give the melting points of these forms I and V. The solid forms of fipronil thus are part of a very complex crystallization scenario. It can be concluded that the melting points given in the literature in no way can indicate which crystalline modification or crystalline modification mixtures were analyzed.

In T 605/02, the Technical Board of Appeal of the European Patent Authority ruled that, in the absence of a respective described preparation procedure, even the XRD pattern of a certain crystalline modification does not constitute prior art for lack of enablement. Thus, melting points given in documents published prior to the filing of this application cannot be regarded as prior art for the present invention as they do not enable the artisan to prepare the novel crystalline modification of fipronil.

The novel crystalline modification V of fipronil is present in a triclinic system having the centrosymmetric space group P-1 (herein also referred to as "crystalline modification V", or "modification V", or "crystalline modification"). Crystalline modification V of fipronil in an X-ray powder diffraction diagram recorded using Cu—Kα radiation (1.54178 Å) at 25°

C. shows at least 3, preferably all of the following reflections quoted below as reflections quoted below as interplanar spacings d or as 2θ values:

$$d=8.55\pm0.1 \text{ Å } 2\theta=10.3\pm0.2° \quad (1)$$

$$d=7.94\pm0.07 \text{ Å } 2\theta=11.1\pm0.2° \quad (2)$$

$$d=6.78\pm0.05 \text{ Å } 2\theta=13.0\pm0.2° \quad (3)$$

$$d=5.43\pm0.05 \text{ Å } 2\theta=16.2\pm0.2° \quad (4)$$

$$d=4.35\pm0.05 \text{ Å } 2\theta=20.3\pm0.2° \quad (5)$$

$$d=2.83\pm0.03 \text{ Å } 2\theta=31.5\pm0.2°. \quad (6)$$

In a particularly preferred embodiment, the crystalline modification V exhibits a powder X-ray diffraction pattern substantially the same as the pattern shown in FIG. 1.

Studies of single crystals of the crystalline modification V have shown that the basic crystal structure is triclinic and has the space group P-1. The characteristic data of the crystal structure of the crystalline modification V are shown in Table 1:

TABLE 1

Crystallographic data of the crystalline modification V

| Parameter | Modification V |
|---|---|
| Class | Triclinic |
| Space group | P-1 |
| a | 8.676(4) Å |
| b | 9.164(4) Å |
| c | 11.367(4) Å |
| α | 73.362(7)° |
| β | 87.216(8)° |
| γ | 83.450(8)° |
| Volume | 860.2(6) Å$^3$ |
| Z | 2 |
| Temperature | −173.2° C. |
| Density (calculated) | 1.73 g/cm$^3$ |
| R1, ωR2 | 0.075, 0.243 | a, b, c = Length of the unit cell edges
α, β, γ = Angles of the unit cell
Z = Number of molecules in the unit cell The crystalline modification V of fipronil has typically a melting point in the range from 200 to 204° C., especially in the range from 201 to 204° C., most preferably at 203° C.

The differential scanning calorimetry (DSC) thermogram of the crystalline modification V of fipronil contains an endotherm with an onset temperature of 202° C. and a maximum of 203° C. The DSC-trace is shown in FIG. 2.

In another embodiment, the present invention relates to the crystalline modification V having a fipronil content of at least 92% by weight, particularly at least 96% by weight and especially at least 98% by weight.

This invention also relates to solid (compositions of) fipronil comprising the crystalline modification V as defined hereinabove and a form of fipronil being different from said crystalline modification V (herein also referred to as "fipronil form"), e.g. amorphous fipronil or fipronil of a crystalline modification different from crystalline modification V. Preferably, the solid (compositions of) fipronil comprise the crystalline modification V in at least 85% by weight, preferably in at least 90% by weight, more preferably in at least 95% by weight, and most preferably in at least 98% by weight. Such compositions of fipronil provide for excellent formulation stability.

The crystalline modification V can be prepared using a process which comprises the following steps:

step i) preparing a solution of a solid form of fipronil being different from the crystalline modification V in a solvent S selected from hot dimethylsulfoxide or hot acetonitrile;

step ii) effecting crystallization of fipronil from the hot solution; and step iii) isolating the resulting precipitate.

A detailed description of these steps is as follows:

Step i)

Suitable fipronil forms different from the crystalline modification V used in step i) are, for example, selected from amorphous fipronil or crystalline fipronil such as monoclinic fipronil of the space group C2/c, monoclinic fipronil of the space group P2$_1$/c, and also mixtures of crystalline modifications of fipronil.

The fipronil form used as starting material in step i) preferably has a purity of at least 85% by weight, in particular at least 90% by weight and especially at least 95% by weight. "Purity" means the absence of chemical compounds other than fipronil.

The solvent S used in step i) consists of either hot dimethylsulfoxide or hot acetonitrile. "Hot" means, in the case of dimethylsulfoxide, a temperature in the range of 100° C. to 150° C., most preferably in the range of 130° C. to 150° C., especially 137° C. to 143° C. In the case of acetonitrile, "hot" means a temperature in the range of 60° C. to 80° C., preferably in the range of 60° C. to 81° C., and most preferably in the range of 70° C. to 81° C., especially 75 to 81° C. Acetonitrile has a boiling point of 81° C.

In a preferred embodiment, the solvent S used in step i) consists of hot dimethylsulfoxide.

In another preferred embodiment, the solvent S used in step i) consists of hot acetonitrile.

In step i), the fipronil form different from the crystalline modification V will usually be incorporated into the solvent S as a solid with mixing at a concentration and temperature where the solvent S is capable of completely dissolving the fipronil form.

The amount of fipronil form dissolved in the solvent S depends, of course, on the nature of the solvent S and on the dissolution temperature. The person skilled in the art will be able to determine suitable conditions by standard experiments.

Step ii)

In step ii) of the process of this invention, fipronil is then crystallized.

Crystallization can be effected in a customary manner, for example by adding a solvent which reduces the solubility or by concentrating the solution, or by a combination of these measures.

In a preferred embodiment, step ii) is carried out in the presence of seed crystals of the crystalline modification V.

To achieve a conversion into the crystalline modification V which is as complete as possible, the crystallization is carried out over a period (duration of crystallization) of at least 1 day, in particular at least 3 days. Duration of crystallization is understood by the person skilled in the art as meaning the period of time between the beginning of the measure which initiates crystallization and the isolation of the fipronil by separating the crystalline material from the mother liquor.

In general, the crystallization is allowed to proceed to a point where at least 60%, preferably at least 70%, in particular at least 90% by weight, for example from 80 to 90% by weight, of the fipronil employed has crystallized out.

Concentration of the solution is effected by gradually removing the solvent S, such as by evaporation in vacuo, and/or in the presence of a flow of an inert gas such as nitrogen or argon. For example, in case where the solvent S consists of dimethylsulfoxide, evaporation is preferably done at 135 to 145° C. in a nitrogen flow.

In a preferred embodiment, the crystallization is effected by concentrating the solution.

Step iii)

In step iii) of the process of this invention, the crystalline modification V is isolated using customary techniques for separating solid components from liquids, for example by filtration, centrifugation or decanting. In general, the isolated precipitate will be washed, for example with the solvent S used for the crystallization. The washing can be carried out in one or more steps. The washing is typically carried out at temperatures lower than 30° C. and in particular lower than 25° C., to keep the loss of the product of value as low as possible. The resulting crystalline fipronil or modification V can then be dried and subjected to further processing.

The preparation process consisting of steps i) to step iii) can be repeated in order to achieve higher purities of fipronil.

Further, crystalline modification V can be prepared by heating crystalline modifications II or $IV_{[B3]}$ at least at 110° C., preferably in between 130° C. and 150° C.

The crystalline modification V is especially suitable for efficiently combating the following pests:

millipedes (Diplopoda) such as *Blaniulus* or *Narceus* ssp; insects (Insecta) such as:

ants, bees, wasps, sawflies (Hymenoptera), e.g. *Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pheidole megacephala, Pogonomyrmex* species such as *Pogonomyrmex barbatus* and *Pogonomyrmex californicus, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* beetles (Coleoptera), such as *Agrilus sinuatus, Agriotes lineatus, Agriotes obscurus* and other *Agriotes* species, *Amphimallus solstitialis, Anisandrus dispar, Anthonomus grandis, Anthonomus pomorum, Aracanthus morei, Atomaria linearis, Blapstinus* species, *Blastophagus piniperda, Blitophaga undata, Bothynoderes punciventris, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus* and other *Conoderus* species, *Conorhynchus mendicus, Crioceris asparagi, Cylindrocopturus adspersus, Diabrotica (longicornis) barberi, Diabrotica semi-punctata, Diabrotica speciosa, Diabrotica undecim-punctata, Diabrotica virgifera* and other *Diabrotica* species, *Eleodes* species, *Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus* and other *Limonius* species, *Lissorhoptrus oryzophilus, Listronotus bonariensis, Melanotus communis* and other *Melanotus* species, *Meligethes aeneus, Melolontha hippocastani, Melolontha melolontha, Oulema oryzae, Ortiorrhynchus sulcatus, Oryzophagus oryzae, Otiorrhynchus ovatus, Oulema oryzae, Phaedon cochleariae, Phyllotreta chrysocephala, Phyllophaga cuyabana* and other *Phyllophaga* species, *Phyllopertha horticola, Phyllotreta nemorum, Phyllotreta striolata,* and other *Phyllotreta* species, *Popillia japonica, Promecops carinicollis, Premnotrypes voraz, Psylliodes* species, *Sitona lineatus, Sitophilus granaria, Sternechus pinguis, Sternechus subsignatus,* and *Tanymechus palliatus* and other *Tanymechus* species, Centipedes (Chilopoda), e.g. *Scutigera coleoptrata,*

Cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,*

Crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,* fleas (Siphonaptera), e.g. *Ctenocephalides felis, Ctenocephalides canis, Xenopsylla cheopis, Pulex irritans, Tunga penetrans,* and *Nosopsyllus fasciatus,*

Flies, mosquitoes (Diptera), e.g. *Aedes aegypti, Aedes albopictus, Aedes vexans, Agromyza oryzae, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Contarinia sorghicola, Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Gasterophilus intestinalis, Geomyza Tripunctata, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Liriomyza sativae, Liriomyza trifolii, Lucilia caprina, Lucilia cuprina, Lucilia sericata, Lycoria pectoralis, Mansonia* spp., *Mayetiola destructor, Musca domestica, Muscina stabulans, Oestrus ovis, Oestrus ovis, Opomyza florum, Oscinella frit, Pegomya hysocyami, Phlebotomus argentipes, Phorbia antiqua, Phorbia brassicae, Phorbia coarctata, Progonya leyoscianii, Psila rosae, Psorophora columbiae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola, Tabanus similis, Tetanops myopaeformis, Tipula olerace,* and *Tipula paludosa,*

Heteropterans (Heteroptera), such as *Acrosternum hilare, Blissus leucopterus,* Cicadellidae such as *Empoasca fabae,* Chrysomelidae, *Cyrtopeltis notatus,* Delpahcidae, *Dysdercus cingulatus, Dysdercus intermedius, Eurygaster integriceps, Euschistus impictiventris, Leptoglossus phyllopus, Lygus lineolaris, Lygus pratensis, Nephotettix* species, *Nezara viridula,* Pentatomidae, *Piesma quadrata, Solubea insularis* and *Thyanta perditor,*

Aphids and other homopterans (Homoptera), e.g. *Acyrthosiphon onobrychis, Adelges laricis, Aphidula nasturtii, Aphis fabae, Aphis forbesi, Aphis glycines, Aphis gossypii, Aphis grossulariae, Aphis pomi, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii,*

*Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes (Myzus) persicae, Myzus ascalonicus, Myzus cerasi, Myzus varians, Nasonovia ribis-nigri, Nilaparvata lugens, Pemphigus bursarius, Pemphigus populivenae*, and other *Pemphigus* species, *Perkinsiella saccharicida, Phorodon humuli*, Psyllidae such as *Psylla mali, Psylla piri* and other *Psylla* species, *Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii*, Lepidopterans (Lepidoptera), for example *Agrotis ypsilon, Agrotis segetum* and other *Agrotis* species, *Alabama argillacea, Anticarsia gemmatalis, Argyresthia conjugella, Autographa gamma, Bupalus piniarius, Cacoecia murinana, Capua reticulana, Cheimatobia brumata, Chilo suppresalis* and other *Chilo* species, *Choristoneura fumiferana, Choristoneura occidentalis, Cirphis unipuncta, Cnaphlocrocis medinalis, Cydia pomonella, Dendrolimus pini, Diaphania nitidalis, Diatraea grandiosella, Earias insulana, Elasmopalpus lignosellus, Eupoecilia ambiguella, Euxoa* species, *Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Lerodea eufala, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae*, Momphidae, *Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sesamia nonagrioides* and other *Sesamia* species, *Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, orthopterans (Orthoptera), such as Acrididae, *Acheta domestica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus* and *Tachycines asynamorus*, silverfish, firebrat (Thysanura), e.g. *Lepisma saccharina* and *Thermobia domestica*, termites (Isoptera), such as *Calotermes flavicollis, Coptotermes* ssp., *Dalbulus maidis, Heterotermes aureus, Leucotermes flavipes, Macrotermes gilvus, Reticulitermes* ssp., *Termes natalensis, Coptotermes formosanus*, thrips (Thysanoptera), such as *Frankliniella fusca, Frankliniella occidentalis, Frankliniella tritici* and other *Franklin-*

*iella* species, *Scirtothrips citri, Thrips oryzae, Thrips palmi, Thrips simplex*, and *Thrips tabaci*, ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, true bugs (Hemiptera), e.g. *Cimex lectularius, Cimex hemipterus, Reduvius senilis, Triatoma* spp., *Rhodnius prolixus*, and *Arilus critatus*, Arachnoidea, such as arachnids (Acarina), for example of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Latrodectus mactans, Loxosceles reclusa, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae species such as *Aculus schlechtendali, Phyllocoptrata oleivora* and *Eriophyes sheldoni*; Tarsonemidae species such as *Phytonemus pallidus* and *Polyphagotarsonemus latus*; Tenuipalpidae species such as *Brevipalpus phoenicis*; Tetranychidae species such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis*, Earwigs (Dermaptera), e.g. *forficula auricularia*; and Nematodes, including plant parasitic nematodes and nematodes living in the soil. Plant parasitic nematodes include, such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species, Dagger nematodes, *Xiphinema* species and other plant parasitic nematode species.

Moreover, the crystalline modification V is especially useful for the control of crop pests, in particular of the Coleoptera, Lepidoptera and Acarina orders.

Moreover, the crystalline modification V is especially useful for the control of non-crop pests (household, turf, ornamental). Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, and Acarina.

For use according to the present invention, the crystalline modification V can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired surfactants (e.g. adjuvans, emulsifiers, dispersing agents), preservatives, antifoaming agents, anti-freezing agents, for seed treatment formulations also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides can be added to the formulation.

Suitable antifoaming agents are for example antifoaming agents based on silicon or magnesium stearate.

Suitable preservatives are for example Dichlorophen und enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, the respective formulations can be diluted 2-10 fold leading to concentrations in the ready to use preparations of 0.01 to 60% by weight active compound by weight, preferably 0.1 to 40% by weight.

The crystalline modification V can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations: 1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 80 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF) (for Seed Treatment Purposes Only)

In an agitated ball mill, 20 parts by weight of the active compound(s) are comminuted with addition of 10 parts by weight of dispersants, 1 part by weight of a gelling agent/wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulation can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l surfactant, 0 to 200 g/l antifreezing agent, 0 to 400 g/l of binder, 0 to 200 g/l of a pigment and up to 1 liter of a solvent, preferably water.

The invention relates in particular to pesticidal or parasiticidal compositions in the form of an aqueous suspension concentrate (SC). Such suspension concentrates comprise the crystalline modification V in a finely divided particulate form, where the particles of the crystalline modification V are suspended in an aqueous medium. The size of the active compound particles, i.e. the size which is not exceeded by 90% by weight of the active compound particles, is typically below 30 μm, in particular below 20 μm. Advantageously, at least 40% by weight and in particular at least 60% by weight of the particles in the SCs according to the invention have diameters below 2 μm.

In addition to the active compound, suspension concentrates typically comprise surfactants, and also, if appropriate, antifoam agents, thickeners, antifreeze agents, stabilizers (biocides), agents for adjusting the pH and anticaking agents.

In such SCs, the amount of active compound, i.e. the total amount of the crystalline modification V and, if appropriate, further active compounds is usually in the range from 10 to 70% by weight, in particular in the range from 20 to 50% by weight, based on the total weight of the suspension concentrate.

Preferred surfactants are anionic and nonionic surfactants. The amount of surfactants will generally be from 0.5 to 20% by weight, in particular from 1 to 15% by weight and particularly preferably from 1 to 10% by weight, based on the total weight of the SCs according to the invention. Preferably, the surfactants comprise at least one anionic surfactant and at least one nonionic surfactant, the ratio of anionic to nonionic surfactant typically being in the range from 10:1 to 1:10.

Examples of anionic surfactants include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and ligno-sulfonates, alkyl phosphates, alkylaryl phosphates, for example tristyryl phosphates, and also polycarboxylates, such as, for example, polyacrylates, maleic anhydride/olefin copolymers (for example Sokalan® CP9, BASF), including the alkali metal, alkaline earth metal, ammonium and amine salts of the substances mentioned above. Preferred anionic surfactants are those which carry at least one sulfonate group, and in particular their alkali metal and their ammonium salts.

Examples of nonionic surfactants comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

In particular, the SCs according to the invention comprise at least one surfactant which improves wetting of the plant parts by the aqueous application form (wetting agent) and at least one surfactant which stabilizes the dispersion of the active compound particles in the SC (dispersant). The amount of wetting agent is typically in the range from 0.5 to 10% by weight, in particular from 0.5 to 5% by weight and especially from 0.5 to 3% by weight, based on the total weight of the SC. The amount of dispersant is typically from 0.5 to 10% by weight and in particular from 0.5 to 5% by weight, based on the total weight of the SC.

Preferred wetting agents are of anionic or nonionic nature and selected, for example, from naphthalenesulfonic acids including their alkali metal, alkaline earth metal, ammonium and amine salts, furthermore fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or nonionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers (for example Sokalan® CP9, BASF), including the alkali metal, alkaline earth metal, ammonium and amine salts of the substances mentioned above.

Viscosity-modifying additives (thickeners) suitable for the SCs according to the invention are in particular compounds which bestow upon the formulation pseudoplastic flow properties, i.e. high viscosity in the resting state and low viscosity in the agitated state. Suitable are, in principle, all compounds used for this purpose in suspension concentrates. Mention may be made, for example, of inorganic substances, such as bentonites or attapulgites (for example Attaclay® from Engelhardt), and organic substances, such as polysaccharides and heteropolysaccharides, such as xanthan gum such as sold under the trademarks Kelzan® from Kelco, Rhodopol® 23 from Rhone Poulenc or Veegum® from R.T. Vanderbilt, and preference is given to using xanthan gum. Frequently, the amount of viscosity-modifying additives is from 0.1 to 5% by weight, based on the total weight of the SC.

Antifoam agents suitable for the SCs according to the invention are, for example, silicone emulsions known for this purpose (Silikon® SRE, from Wacker, or Rhodorsil® from Rhodia), long-chain alcohols, fatty acids, defoamers of the type of aqueous wax dispersions, solid defoamers (so-called Compounds), organofluorine compounds and mixtures thereof. The amount of antifoam agent is typically from 0.1 to 1% by weight, based on the total weight of the SC.

Bactericides may be added for stabilizing the suspension concentrates according to the invention. Suitable bactericides are those based on isothiazolones, for example Proxel® from ICI or Acticide® RS from Thor Chemie or Kathon® MK from Rohm & Haas. The amount of bactericides is typically from 0.05 to 0.5% by weight, based on the total weight of the SC.

Suitable antifreeze agents are liquid polyols, for example ethylene glycol, propylene glycol or glycerol. The amount of antifreeze agents is generally from 1 to 20% by weight, in particular from 5 to 10% by weight, based on the total weight of the suspension concentrate.

If appropriate, the SCs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

The invention relates in particular to pesticidal or parasiticidal compositions in the form of water-dispersible granules (WG) or a water dispersible powder (WP). Such formulations comprise the crystalline modification V in a finely divided particulate form, where the particles of the crystalline modification V are homogenized in a solid or powder form. The size of the active compound particles, i.e. the size which is not exceeded by 90% by weight of the active compound particles, is typically below 30 µm, in particular below 20 µm. Advantageously, at least 40% by weight and in particular at least 60% by weight of the particles in the WGs or WPs according to the invention have diameters below 5 µm.

In addition to the active compound, water-dispersible powders and water dispersible granules typically comprise surfactants, and also, if appropriate, antifoam agents, fillers, binders, and anticaking agents.

In such WGs and WPs, the amount of active compound, i.e. the total amount of the crystalline modification V and, if appropriate, further active compounds is usually in the range from 10 to 90% by weight, in particular in the range from 20 to 75% by weight, based on the total weight of the WG/WP.

Preferred surfactants are anionic and nonionic surfactants. The amount of surfactants will generally be from 0.5 to 20% by weight, in particular from 1 to 15% by weight and particularly preferably from 1 to 10% by weight, based on the total weight of the WGs or WPs according to the invention. Preferably, the surfactants comprise at least one anionic surfactant and at least one nonionic surfactant, the ratio of anionic to nonionic surfactant typically being in the range from 10:1 to 1:10.

Examples of anionic surfactants include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and also polycarboxylates, such as, for example, polyacrylates, maleic anhydride/olefin copolymers (for example Sokalan® CP9, BASF), including the alkali metal, alkaline earth metal, ammonium and amine salts of the substances mentioned above. Preferred anionic surfactants are those which carry at least one sulfonate group, and in particular their alkali metal and their ammonium salts.

Examples of nonionic surfactants comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

In particular, the WGs or WPs according to the invention comprise at least one surfactant which improves wetting of the formulation by the aqueous application form (wetting agent) and at least one surfactant which allows dispersion of the active compound particles in aqueous dilutions. The amount of wetting agent is typically in the range from 0.5 to 10% by weight, in particular from 0.5 to 5% by weight and especially from 0.5 to 3% by weight, based on the total weight of the WG/WP. The amount of dispersant is typically from 0.5 to 10% by weight and in particular from 2.0 to 8% by weight, based on the total weight of the WG/WP.

Preferred wetting agents are of anionic or nonionic nature and selected, for example, from naphthalenesulfonic acids including their alkali metal, alkaline earth metal, ammonium and amine salts, furthermore fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or nonionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, sodium phosphates, sodium lauryl sulphate, modified cellulose gum, polyvinylpyrrolidinone, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/ olefin copolymers (for example Sokalan® CP9, BASF), including the alkali metal, alkaline earth metal, ammonium and amine salts of the substances mentioned above.

Antifoam agents suitable for the WGs or WPs according to the invention are, for example, tallow soap known for this purpose (Agnique Soap L, Foamaster Soap L), long-chain alcohols, fatty acids, organofluorine compounds and mixtures thereof. The amount of antifoam agent is typically from 0.1 to 1% by weight, based on the total weight of the WG/WP.

Fillers, binders, or additional dispersing aids suitable for the WGs and WPs according to the invention typically make up the remainder of the formulation. These typically are for example kaolin or attapulgite clay, fumed or precipitated silica, diatomateous earth, ammonium sulphate, or calcium silicate.

The crystalline modification V is effective through both contact and ingestion.

According to a preferred embodiment of the invention, the crystalline modification V is employed via soil application. Soil application is especially favorable for use against ants, termites, crickets, or cockroaches.

According to another preferred embodiment of the invention, for use against non-crop pests such as ants, termites, wasps, flies, mosquitoes, crickets, locusts, or cockroaches the crystalline modification V is prepared into a bait preparation.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones. Suitable feeding stimulants are chosen, for example, from animal and/or plant proteins (meat-, fish- or blood meal, insect parts, crickets powder, egg yolk), from fats and oils of animal and/or plant origin, or mono-, oligo- or polyorganosaccharides, especially from sucrose, lactose, fructose, dextrose, glucose, starch, pectin or even molasses or honey, or from salts such as ammonium sulfate, ammonium carbonate or ammonium acetate. Fresh or decaying parts of fruits, crops, plants, animals, insects or specific parts thereof can also serve as a feeding stimulant. Pheromones are known to be more insect specific. Specific pheromones are described in the literature and are known to those skilled in the art.

We have found that the pesticidal mixtures solve the problems of reducing the dosage rate and/or enhancing the spectrum of activity and/or combining knock-down activity with prolonged control and/or to resistance management and/or promoting the health of plants.

Compositions of this invention may also contain other active ingredients, for example other pesticides, insecticides, fungicides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

It has been found that a mixture of modification V and at least a pesticidal or fungicidal compound as defined below show markedly enhanced action against pests and/or fungi compared to the control rates that are possible with the individual compounds and/or is suitable for improving the health of plants when applied to plants, parts of plants, seeds, or at their locus of growth.

The following list of pesticidal or parasiticidal compounds which can be used together with the crystalline modification V according to the invention is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, tebufenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula $I'^1$

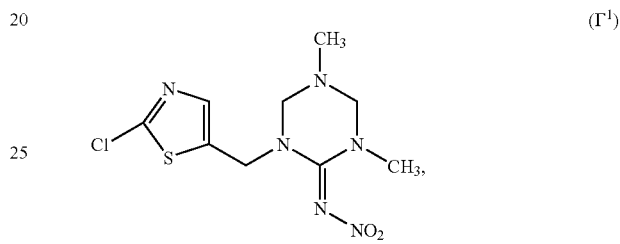

A.6. GABA antagonist compounds: acetoprole, endosulfan, ethiprole, fipronil, vaniliprole, pyrafluprole, pyriprole, 5-Amino-1-(2,6-dichloro-4-trifluoromethyl-phenyl)-4-trifluoromethanesulfinyl-1H-pyrazole-3-carbothioic acid amide of formula $I'^2$

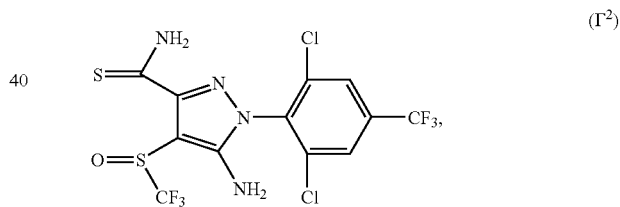

A.7. Macrocyclic lactone insecticides: abamectin, emamectin, milbemectin, lepimectin, spinosad;

A.8. METI I compounds: fenazaquin, pyridaben, tebufenpyrad, tolfenpyrad, flufenerim;

A.9. METI II and III compounds: acequinocyl, fluacyprim, hydramethylnon;

A.10. Uncoupler compounds: chlorfenapyr;

A.11. Oxidative phosphorylation inhibitor compounds: cyhexatin, diafenthiuron, fenbutatin oxide, propargite;

A.12. Moulting disruptor compounds: cyromazine;

A.13. Mixed Function Oxidase inhibitor compounds: piperonyl butoxide;

A.14. Sodium channel blocker compounds: indoxacarb, metaflumizone,

A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the anthranilamide compounds of formula $I'^3$

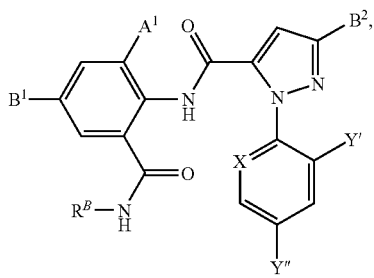

wherein $A^1$ is $CH_3$, Cl, Br, I, X is C—H, C—Cl, C—F or N, Y' is F, Cl, or Br, Y" is hydrogen, F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and the malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl)malononitrile), $CF_3(CH_2)_2C(CN)_2CH_2(CF_2)_5CF_2H$ (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2(CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2 CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5-Nonafluoro-pentyl)-2-(3,3,3-trifluoro-propyl)-malononitrile), $CF_3(CF_2)_2CH_2C(CN)_2CH_2(CF_2)_3 CF_2H$ (2-(2,2,3,3,4,4,4-Heptafluoro-butyl)-2-(2,2,3,3,4,4,5,5-octafluoro-pentyl)-malononitrile) and $CF_3CF_2CH_2C(CN)_2 CH_2(CF_2)_3CF_2H$ (2-(2,2,3,3,4,4,5,5-Octafluoro-pentyl)-2-(2,2,3,3,3-pentafluoro-propyl)-malononitrile).

The commercially available compounds of the group A may be found in The Pesticide Manual, 13$^{th}$ Edition, British Crop Protection Council (2003) among other publications. Thioamides of formula $I'^2$ and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. Anthranilamides of formula $I'^3$ and their preparation have been described in WO 01/70671; WO 02/48137; WO 03/24222, WO 03/15518, WO 04/67528; WO 04/33468; and WO 05/118552. The malononitrile compounds $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl)malononitrile), $CF_3(CH_2)_2C(CN)_2CH_2(CF_2)_5CF_2H$ (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2 (CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2 CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5-Nonafluoro-pentyl)-2-(3,3,3-trifluoro-propyl)-malononitrile), $CF_3(CF_2)_2CH_2C(CN)_2CH_2(CF_2)_3 CF_2H$ (2-(2,2,3,3,4,4,4-Heptafluoro-butyl)-2-(2,2,3,3,4,4,5,5-octafluoro-pentyl)-malononitrile) and $CF_3CF_2CH_2C(CN)_2 CH_2(CF_2)_3CF_2H$ (2-(2,2,3,3,4,4,5,5-Octafluoro-pentyl)-2-(2,2,3,3,3-pentafluoro-propyl)-malononitrile) have been described in WO 05/63694.

The following list of fungicidal compounds which can be used together with the crystalline modification V according to the invention is intended to illustrate the possible combinations, but not to impose any limitation:

Preferred are the binary mixtures containing modification V as compound I.

Preferred are the tertiary mixtures containing modification V as compound I, a compound IIA, and a compound IIB.

Preferred are the quaternary mixtures containing modification V as compound I, a compound IIA, and two compounds IIB1 and IIB2, resp.

Especially preferred are binary mixtures containing modification V as compound I and a fungicidal compound IIA selected from the list comprising azoles: cyproconazole, difenoconazole, epoxiconazole, fenbuconazole, fluquinconazole, flutriafol, hexaconazole, ipconazole, metconazole, propiconazole, prothioconazole, tebuconazole, tetraconazole, triadimenol, triadimefon, triticonazole, cyazofamid, imazalil, prochloraz, triflumizol, benomyl, carbendazim, thiabendazole, ethaboxam, and hymexazole.

Especially preferred are binary mixtures containing modification V as compound I and a fungicidal compound IIA selected from the list comprising strobilurins: azoxystrobin, dimoxystrobin, enestroburin, fluoxastrobin, kresoxim-methyl, metominostrobin, picoxystrobin, pyraclostrobin, trifloxystrobin, methyl (2-chloro-5-[1-(3-methylbenzyloxy-imino)ethyl]benzyl)carbamate, methyl (2-chloro-5-[1-(6-methylpyridin-2-ylmethoxy-imino)ethyl]benzyl)carbamate, and methyl 2-(ortho-((2,5-dimethylphenyloxy-methylene)phenyl)-3-methoxyacrylate;

Especially preferred are binary mixtures containing modification V as compound I and a fungicidal compound IIA selected from the list comprising carboxamides: boscalid, carboxin, benalaxyl, fenhexamid, flutolanil, furametpyr, metalaxyl, mefenoxam (metalaxyl-M), ofurace, oxadixyl, oxycarboxin, penthiopyrad, thifluzamide, tiadinil, dimethomorph, fluopicolide (picobenzamid), diclocymet, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide; 3,4-dichloro-N-(2-cyanophenyl)isothiazol-5-carboxamide; N-(2',4'-difluorobiphenyl-2-yl)-1-methyl-3-trifluoromethyl-1H-pyrazole-4-carboxamide; N-(2',4'-dichlorobiphenyl-2-yl)-1-methyl-3-trifluoromethyl-1H-pyrazole-4-carboxamide; N-(2',4'-difluorobiphenyl-2-yl)-3-difluoromethyl-1-methyl-1H-pyrazole-4-carboxamide; N-(2',4'-dichlorobiphenyl-2-yl)-3-difluoromethyl-1-methyl-1H-pyrazole-4- carboxamide; N-(2',5'-difluorobiphenyl-2-yl)-1-methyl-3-trifluoromethyl-1H-pyrazole-4-carboxamide; N-(2',5'-dichlorobiphenyl-2-yl)-1-methyl-3-trifluoromethyl-1H-pyrazole-4-carboxamide; N-(2',5'-difluorobiphenyl-2-yl)-3-difluoromethyl-1-methyl-1H-pyrazole-4-carboxamide; N-(2',5'-dichlorobiphenyl-2-yl)-3-di-fluoromethyl-1-methyl-1H-pyrazole-4-carboxamide; N-(3',5'-difluoro-biphenyl-2-yl)-1-methyl-3-trifluoromethyl-1H-pyrazole-4-carboxamide; N-(3',5'-dichlorobiphenyl-2-yl)-1-methyl-3-trifluoromethyl-1H-pyrazole-4-carboxamide, N-(3',5'-difluorobiphenyl-2-yl)-3-difluoromethyl-1-methyl-1H-pyrazole-4-carboxamide; N-(3',5'-dichlorobiphenyl-2-yl)-3-difluoromethyl-1-methyl-1H-pyrazole-4-carboxamide; N-(3'-fluorobiphenyl-2-yl)-1-methyl-3-trifluoro-methyl-1H-pyrazole-4-carboxamide, N-(3'-chlorobiphenyl-2-yl)-1-methyl-3-trifluoromethyl-1H-pyrazole-4-carboxamide; N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide; N-(2'-fluorobiphenyl-2-yl)-1-methyl-3-trifluoromethyl-1H-pyrazole-4-carboxamide; N-(2'-chlorobiphenyl-2-yl)-1-methyl-3-trifluoro-methyl-1H-pyrazole-4-carboxamide; N-(2'-fluorobiphenyl-2-yl)-3-difluoro-methyl-1-methyl-1H-pyrazole-4-carboxamide; N-(2'-chlorbiphenyl-2-yl)-3-difluoromethyl-1-methyl-1H-pyrazole-4-carboxamide; N-(2'-fluoro-4'-chloro-5'-methylbiphenyl-2-yl)-1-methyl-3-trifluoromethyl-1H-pyrazole-4-carbox-amide; N-(3',4',5'-trifluorobiphenyl-2-yl)-1-methyl-3-trifluoromethyl-1H-pyrazole-4-carboxamide; N-(3',4',5'-trifluorobiphenyl-2-yl)-1-methyl-3-difluoromethyl-1H-pyrazole-4-carboxamide; N-(2',4',5'-trifluorobiphenyl-2-yl)-1-methyl-3-difluoromethyl-1H-pyrazole-4-carboxamide; N-(3',4',5'-tri-fluorobiphenyl-2-yl)-3-chlorofluoromethyl-1-methyl-1H-pyrazole-4-carbox-amide; N-[2-(1,1,2,3,3,3-hexa-fluoropropoxy)phenyl]-1-methyl-3-trifluoro-methyl-1H-pyrazole-4-carboxamide; N-[2-(1,1,2,3,3,3-hexafluor-opropoxy)phenyl]-3-difluoromethyl-1-methyl-1H-pyrazole-4-carboxamide, N-[2-(2-chloro-1,1,2-trifluoroethoxy)phenyl]-1-methyl-3-trifluoromethyl-1H-pyrazole-4-carboxamide; N-[2-(2-chlor-1,1,2-trifluoroethoxy)phenyl]-3-difluoro-methyl-1-methyl-1H-pyrazole-4-carboxamide; N-[2-(1,1,2,2-tetra-fluoroethoxy)phenyl]-3-difluoromethyl-1-methyl-1H-pyrazole-4-carbox-amide; N-[2-(1,1,2,2-tetrafluoro-ethoxy)phenyl]-1-methyl-3-trifluoro-methyl-1H-pyrazole-4-carboxamide; N-(4'-(trifluoro-methylthio)biphenyl-2-yl)-3-di-fluoromethyl-1-methyl-1H-pyrazole-4-carboxamide; N-(4'-(trifluoromethyl-thio)biphenyl-2-yl)-1-methyl-3-trifluoromethyl-1H-pyrazole-4-carboxamide; and 5-fluoro-1,3-dimethyl-1H-pyrazole-4-carboxylic acid [2-(1,2-dimethyl-propyl)-phenyl]-amide.

Especially preferred are binary mixtures containing modification V as compound I and a fungicidal compound IIA selected from the list comprising heterocylic compounds: pyrimethanil, fenpiclonil, fludioxonil, aldimorph, dodemorph, fenpropimorph, tridemorph, iprodione, procymidone, famoxadone, fenamidone, octhilinone, probenazole, diclomezine, pyroquilon, proquinazid, tricyclazole, captafol, captan, dazomet, fenoxanil, quinoxyfen, 5-chloro-7-(4-methylpiperidin-1-yl)-6-(2,4,6-trifluorophenyl)-[1,2,4]triazolo[1,5-a]pyrimidine, 6-(3,4-dichloro-phenyl)-5-methyl-[1,2,4]triazolo[1,5-a]pyrimidine-7-ylamine, 6-(4-tert-butylphenyl)-5-methyl-[1,2,4]triazolo[1,5-a]pyrimidine-7-ylamine, 5-methyl-6-(3,5,5-trimethyl-hexyl)-[1,2,4]triazolo[1,5-a]pyrimidine-7-ylamine, 5-methyl-6-octyl-[1,2,4]triazolo[1,5-a]pyrimi-dine-7-ylamine, 6-methyl-5-octyl-[1,2,4]triazol[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethyl-hexyl)-[1,2,4]triazolo[1,5-a]pyrimidine-7-ylamine, 6-octyl-5-propyl-[1,2,4]tri-azolo[1,5-a]pyrimidine-7-ylamine, 5-methoxymethyl-6-octyl-[1,2,4]tri-azolo[1,5-a]pyrimidine-7-ylamine, 6-octyl-5-trifluoromethyl-[1,2,4]tri-azolo[1,5-a]pyrimidine-7-ylamine, and 5-trifluoro-methyl-6-(3,5,5-trimethyl-hexyl)-[1,2,4]triazolo[1,5-a]pyrimidine-7-ylamine.

Especially preferred are binary mixtures containing modification V as compound I and a fungicidal compound IIA selected from the list comprising carbamates: mancozeb, maneb, metam, metiram, ferbam, propineb, thiram, zineb, ziram; diethofencarb, iprovalicarb, propamocarb, and methyl 3-(4-chlorophenyl)-3-(2-isopropoxycarbonylamino-3-methylbutyrylamino)propanoate.

Especially preferred are binary mixtures containing modification V as compound I and a fungicidal compound IIA selected from the list comprising: guazatine; streptomycin, validamycin A; binapacryl, dinocap, dinobuton; dithianon, isoprothiolane; fentin salts, such as fentin-acetate; edifenphos, iprobenfos, fosetyl, pyrazophos, chlorothalonil, dichlofluanid, flusulfamide, phthalide, quintozene, thiophanate-methyl, tolylfluanid; copper acetate, copper hydroxide, copper oxychloride, basic copper sulfate, sulfur; cyflufenamid, cymoxanil, dimethirimol, ethirimol, furalaxyl, metrafenone, and spiroxamine.

The active compounds IIA mentioned above, their preparation and their action against harmful fungi are generally known (cf.: http://www.hclrss.demon.co.uk/index.html); they are commercially available. The compounds named according to IUPAC, their preparation and their fungicidal activity are likewise known from EP-A 12 01 648; EP-A 226 917; WO 98/46608; WO 99/24413; WO 2004/049804; WO 2003/066609; WO 2003/053145; WO 2003/14103; EP-A 10 35 122; EP-A 10 28 125; EP-A 71 792; EP-A 141 317; WO 2003/009687; WO 05/087771; WO 2005/087772; WO 2005/087773; WO 2006/087325; WO 2006/087325; WO 2006/092428; WO 2006/092428; WO 2006/087343; WO 2001/42223; WO 2005/34628; WO 2005/123689; WO 2005/123690; WO 2006/120219; PCT/EP2006/064991; WO 2007/017450, and EP Application No. 06123463.9

With respect to their intended use, the following tertiary and quaternary mixtures of modification V as compound I are especially preferred:

Table1
Mixtures wherein compound IIA is trifloxystrobin, and the combination of compounds IIB1 and IIB2 in each case corresponds to a row of Table Q.

Table2
Mixtures wherein compound IIA is azoxystrobin, and the combination of compounds IIB1 and IIB2 in each case corresponds to a row of Table Q.

Table3
Mixtures wherein compound IIA is pyraclostrobin, and the combination of compounds IIB1 and IIB2 in each case corresponds to a row of Table Q.

Table4
Mixtures wherein compound IIA is boscalid, and the combination of compounds IIB1 and IIB2 in each case corresponds to a row of Table Q.

Table5
Mixtures wherein compound IIA is metalaxyl, and the combination of compounds IIB1 and IIB2 in each case corresponds to a row of Table Q.

Table 6
Mixtures wherein compound IIA is metalaxyl-M, and the combination of compounds IIB1 and IIB2 in each case corresponds to a row of Table Q.

Table 7
Mixtures wherein compound IIA is cyproconazole, and the combination of compounds IIB1 and IIB2 in each case corresponds to a row of Table Q.

Table 8
Mixtures wherein compound IIA is epoxiconazole, and the combination of compounds IIB1 and IIB2 in each case corresponds to a row of Table Q.

Table 9
Mixtures wherein compound IIA is fenbuconazole, and the combination of compounds IIB1 and IIB2 in each case corresponds to a row of Table Q.

Table 10
Mixtures wherein compound IIA is fluquinconazole, and the combination of compounds IIB1 and IIB2 in each case corresponds to a row of Table Q.

Table 11
Mixtures wherein compound IIA is flutriafol, and the combination of compounds IIB1 and IIB2 in each case corresponds to a row of Table Q.

Table 12
Mixtures wherein compound IIA is ipconazole, and the combination of compounds IIB1 and IIB2 in each case corresponds to a row of Table Q.

Table 13
Mixtures wherein compound IIA is metconazole, and the combination of compounds IIB1 and IIB2 in each case corresponds to a row of Table Q.

Table 14
Mixtures wherein compound IIA is propiconazole, and the combination of compounds IIB1 and IIB2 in each case corresponds to a row of Table Q.

Table 15
Mixtures wherein compound IIA is prothioconazole, and the combination of compounds IIB1 and IIB2 in each case corresponds to a row of Table Q.

Table 16
Mixtures wherein compound IIA is tebuconazole, and the combination of compounds IIB1 and IIB2 in each case corresponds to a row of Table Q.

Table 17
Mixtures wherein compound IIA is triadimenol, and the combination of compounds IIB1 and IIB2 in each case corresponds to a row of Table Q.

Table 18
Mixtures wherein compound IIA is triticonazole, and the combination of compounds IIB1 and IIB2 in each case corresponds to a row of Table Q.

Table 19
Mixtures wherein compound IIA is imazalil, and the combination of compounds IIB1 and IIB2 in each case corresponds to a row of Table Q.

Table 20
Mixtures wherein compound IIA is prochloraz, and the combination of compounds IIB1 and IIB2 in each case corresponds to a row of Table Q.

Table 21
Mixtures wherein compound IIA is carbendazim, and the combination of compounds IIB1 and IIB2 in each case corresponds to a row of Table Q.

Table 22
Mixtures wherein compound IIA is thiabendazole, and the combination of compounds IIB1 and IIB2 in each case corresponds to a row of Table Q.

Table 23
Mixtures wherein compound IIA is ethaboxam, and the combination of compounds IIB1 and IIB2 in each case corresponds to a row of Table Q.

Table 24
Mixtures wherein compound IIA is hymexazole, and the combination of compounds IIB1 and IIB2 in each case corresponds to a row of Table Q.

Table 25
Mixtures wherein compound IIA is pyrimethanil, and the combination of compounds IIB1 and IIB2 in each case corresponds to a row of Table Q.

Table 26
Mixtures wherein compound IIA is fludioxonil, and the combination of compounds IIB1 and IIB2 in each case corresponds to a row of Table Q.

Table 27
Mixtures wherein compound IIA is aldimorph, and the combination of compounds IIB1 and IIB2 in each case corresponds to a row of Table Q.

Table 28
Mixtures wherein compound IIA is dodemorph, and the combination of compounds IIB1 and IIB2 in each case corresponds to a row of Table Q.

Table 29
Mixtures wherein compound IIA is fenpropimorph, and the combination of compounds IIB1 and IIB2 in each case corresponds to a row of Table Q.

Table 30
Mixtures wherein compound IIA is iprodione, and the combination of compounds IIB1 and IIB2 in each case corresponds to a row of Table Q.

Table 31
Mixtures wherein compound IIA is captan, and the combination of compounds IIB1 and IIB2 in each case corresponds to a row of Table Q.

Table 32
Mixtures wherein compound IIA is fenoxanil, and the combination of compounds IIB1 and IIB2 in each case corresponds to a row of Table Q.

Table 33
Mixtures wherein compound IIA is probenazole, and the combination of compounds IIB1 and IIB2 in each case corresponds to a row of Table Q.

Table 34
Mixtures wherein compound IIA is mancozeb, and the combination of compounds IIB1 and IIB2 in each case corresponds to a row of Table Q.

Table 35
Mixtures wherein compound IIA is metiram, and the combination of compounds IIB1 and IIB2 in each case corresponds to a row of Table Q.

Table 36
Mixtures wherein compound IIA is thiram, and the combination of compounds IIB1 and IIB2 in each case corresponds to a row of Table Q.

Table 37
Mixtures wherein compound IIA is ziram, and the combination of compounds IIB1 and IIB2 in each case corresponds to a row of Table Q.

Table 38
Mixtures wherein compound IIA is guazatin, and the combination of compounds IIB1 and IIB2 in each case corresponds to a row of Table Q.

Table39

Mixtures wherein compound IIA is thiophanate-methyl, and the combination of compounds IIB1 and IIB2 in each case corresponds to a row of Table Q.

Table40

Mixtures wherein compound IIA is chlorothalonil, and the combination of compounds IIB1 and IIB2 in each case corresponds to a row of Table Q.

Table41

Mixtures wherein compound IIA is metrafenone, and the combination of compounds IIB1 and IIB2 in each case corresponds to a row of Table Q.

TABLE Q

| Mixture No. | Compound IIB1 | Compound IIB2 |
|---|---|---|
| M-1 | azoxystrobin | — |
| M-2 | azoxystrobin | boscalid |
| M-3 | azoxystrobin | metalaxyl |
| M-4 | azoxystrobin | cyproconazole |
| M-5 | azoxystrobin | epoxiconazole |
| M-6 | azoxystrobin | fenbuconazole |
| M-7 | azoxystrobin | fluquinconazole |
| M-8 | azoxystrobin | flutriafol |
| M-9 | azoxystrobin | ipconazole |
| M-10 | azoxystrobin | metconazole |
| M-11 | azoxystrobin | propiconazole |
| M-12 | azoxystrobin | prothioconazole |
| M-13 | azoxystrobin | tebuconazole |
| M-14 | azoxystrobin | triadimenol |
| M-15 | azoxystrobin | triticonazole |
| M-16 | azoxystrobin | imazalil |
| M-17 | azoxystrobin | prochloraz |
| M-18 | azoxystrobin | carbendazim |
| M-19 | azoxystrobin | thiabendazole |
| M-20 | azoxystrobin | ethaboxam |
| M-21 | azoxystrobin | hymexazole |
| M-22 | azoxystrobin | pyrimethanil |
| M-23 | azoxystrobin | fludioxonil |
| M-24 | azoxystrobin | aldimorph |
| M-25 | azoxystrobin | dodemorph |
| M-26 | azoxystrobin | fenpropimorph |
| M-27 | azoxystrobin | iprodione |
| M-28 | azoxystrobin | captan |
| M-29 | azoxystrobin | fenoxanil |
| M-30 | azoxystrobin | probenazol |
| M-31 | azoxystrobin | mancozeb |
| M-32 | azoxystrobin | metiram |
| M-33 | azoxystrobin | thiram |
| M-34 | azoxystrobin | ziram |
| M-35 | azoxystrobin | guazatin |
| M-36 | azoxystrobin | thiophanate-methyl |
| M-37 | azoxystrobin | chlorothalonil |
| M-38 | azoxystrobin | metrafenone |
| M-39 | trifloxystrobin | — |
| M-40 | trifloxystrobin | boscalid |
| M-41 | trifloxystrobin | metalaxyl |
| M-42 | trifloxystrobin | cyproconazole |
| M-43 | trifloxystrobin | epoxiconazole |
| M-44 | trifloxystrobin | fenbuconazole |
| M-45 | trifloxystrobin | fluquinconazole |
| M-46 | trifloxystrobin | flutriafol |
| M-47 | trifloxystrobin | ipconazole |
| M-48 | trifloxystrobin | metconazole |
| M-49 | trifloxystrobin | propiconazole |
| M-50 | trifloxystrobin | prothioconazole |
| M-51 | trifloxystrobin | tebuconazole |
| M-52 | trifloxystrobin | triadimenol |
| M-53 | trifloxystrobin | triticonazole |
| M-54 | trifloxystrobin | imazalil |
| M-55 | trifloxystrobin | prochloraz |
| M-56 | trifloxystrobin | carbendazim |
| M-57 | trifloxystrobin | thiabendazole |
| M-58 | trifloxystrobin | ethaboxam |
| M-59 | trifloxystrobin | hymexazole |
| M-60 | trifloxystrobin | pyrimethanil |
| M-61 | trifloxystrobin | fludioxonil |
| M-62 | trifloxystrobin | aldimorph |
| M-63 | trifloxystrobin | dodemorph |
| M-64 | trifloxystrobin | fenpropimorph |
| M-65 | trifloxystrobin | iprodione |
| M-66 | trifloxystrobin | captan |
| M-67 | trifloxystrobin | fenoxanil |
| M-68 | trifloxystrobin | probenazol |
| M-69 | trifloxystrobin | mancozeb |
| M-70 | trifloxystrobin | metiram |
| M-71 | trifloxystrobin | thiram |
| M-72 | trifloxystrobin | ziram |
| M-73 | trifloxystrobin | guazatin |
| M-74 | trifloxystrobin | thiophanate-methyl |
| M-75 | trifloxystrobin | chlorothalonil |
| M-76 | trifloxystrobin | metrafenone |
| M-77 | orysastrobin | — |
| M-78 | orysastrobin | boscalid |
| M-79 | orysastrobin | metalaxyl |
| M-80 | orysastrobin | cyproconazole |
| M-81 | orysastrobin | epoxiconazole |
| M-82 | orysastrobin | fenbuconazole |
| M-83 | orysastrobin | fluquinconazole |
| M-84 | orysastrobin | flutriafol |
| M-85 | orysastrobin | ipconazole |
| M-86 | orysastrobin | metconazole |
| M-87 | orysastrobin | propiconazole |
| M-88 | orysastrobin | prothioconazole |
| M-89 | orysastrobin | tebuconazole |
| M-90 | orysastrobin | triadimenol |
| M-91 | orysastrobin | triticonazole |
| M-92 | orysastrobin | imazalil |
| M-93 | orysastrobin | prochloraz |
| M-94 | orysastrobin | carbendazim |
| M-95 | orysastrobin | thiabendazole |
| M-96 | orysastrobin | ethaboxam |
| M-97 | orysastrobin | hymexazole |
| M-98 | orysastrobin | pyrimethanil |
| M-99 | orysastrobin | fludioxonil |
| M-100 | orysastrobin | aldimorph |
| M-101 | orysastrobin | dodemorph |
| M-102 | orysastrobin | fenpropimorph |
| M-103 | orysastrobin | iprodione |
| M-104 | orysastrobin | captan |
| M-105 | orysastrobin | fenoxanil |
| M-106 | orysastrobin | probenazol |
| M-107 | orysastrobin | mancozeb |
| M-108 | orysastrobin | metiram |
| M-109 | orysastrobin | thiram |
| M-110 | orysastrobin | ziram |
| M-111 | orysastrobin | guazatin |
| M-112 | orysastrobin | thiophanate-methyl |
| M-113 | orysastrobin | chlorothalonil |
| M-114 | orysastrobin | metrafenone |
| M-115 | pyraclostrobin | — |
| M-116 | pyraclostrobin | boscalid |
| M-117 | pyraclostrobin | metalaxyl |
| M-118 | pyraclostrobin | cyproconazole |
| M-119 | pyraclostrobin | epoxiconazole |
| M-120 | pyraclostrobin | fenbuconazole |
| M-121 | pyraclostrobin | fluquinconazole |
| M-122 | pyraclostrobin | flutriafol |
| M-123 | pyraclostrobin | ipconazole |
| M-124 | pyraclostrobin | metconazole |
| M-125 | pyraclostrobin | propiconazole |
| M-126 | pyraclostrobin | prothioconazole |
| M-127 | pyraclostrobin | tebuconazole |
| M-128 | pyraclostrobin | triadimenol |
| M-129 | pyraclostrobin | triticonazole |
| M-130 | pyraclostrobin | imazalil |
| M-131 | pyraclostrobin | prochloraz |
| M-132 | pyraclostrobin | carbendazim |
| M-133 | pyraclostrobin | thiabendazole |
| M-134 | pyraclostrobin | ethaboxam |
| M-135 | pyraclostrobin | hymexazole |

TABLE Q-continued

| Mixture No. | Compound IIB1 | Compound IIB2 |
|---|---|---|
| M-136 | pyraclostrobin | pyrimethanil |
| M-137 | pyraclostrobin | fludioxonil |
| M-138 | pyraclostrobin | aldimorph |
| M-139 | pyraclostrobin | dodemorph |
| M-140 | pyraclostrobin | fenpropimorph |
| M-141 | pyraclostrobin | iprodione |
| M-142 | pyraclostrobin | captan |
| M-143 | pyraclostrobin | fenoxanil |
| M-144 | pyraclostrobin | probenazol |
| M-145 | pyraclostrobin | mancozeb |
| M-146 | pyraclostrobin | metiram |
| M-147 | pyraclostrobin | thiram |
| M-148 | pyraclostrobin | ziram |
| M-149 | pyraclostrobin | guazatin |
| M-150 | pyraclostrobin | thiophanate-methyl |
| M-151 | pyraclostrobin | chlorothalonil |
| M-152 | pyraclostrobin | metrafenone |
| M-153 | boscalid | — |
| M-154 | boscalid | metalaxyl |
| M-155 | boscalid | cyproconazole |
| M-156 | boscalid | epoxiconazole |
| M-157 | boscalid | fenbuconazole |
| M-158 | boscalid | fluquinconazole |
| M-159 | boscalid | flutriafol |
| M-160 | boscalid | ipconazole |
| M-161 | boscalid | metconazole |
| M-162 | boscalid | propiconazole |
| M-163 | boscalid | prothioconazole |
| M-164 | boscalid | tebuconazole |
| M-165 | boscalid | triadimenol |
| M-166 | boscalid | triticonazole |
| M-167 | boscalid | imazalil |
| M-168 | boscalid | prochloraz |
| M-169 | boscalid | carbendazim |
| M-170 | boscalid | thiabendazole |
| M-171 | boscalid | ethaboxam |
| M-172 | boscalid | hymexazole |
| M-173 | boscalid | pyrimethanil |
| M-174 | boscalid | fludioxonil |
| M-175 | boscalid | aldimorph |
| M-176 | boscalid | dodemorph |
| M-177 | boscalid | fenpropimorph |
| M-178 | boscalid | iprodione |
| M-179 | boscalid | captan |
| M-180 | boscalid | fenoxanil |
| M-181 | boscalid | probenazol |
| M-182 | boscalid | mancozeb |
| M-183 | boscalid | metiram |
| M-184 | boscalid | thiram |
| M-185 | boscalid | ziram |
| M-186 | boscalid | guazatin |
| M-187 | boscalid | thiophanate-methyl |
| M-188 | boscalid | chlorothalonil |
| M-189 | boscalid | metrafenone |
| M-190 | metalaxyl | — |
| M-191 | metalaxyl | cyproconazole |
| M-192 | metalaxyl | epoxiconazole |
| M-193 | metalaxyl | fenbuconazole |
| M-194 | metalaxyl | fluquinconazole |
| M-195 | metalaxyl | flutriafol |
| M-196 | metalaxyl | ipconazole |
| M-197 | metalaxyl | metconazole |
| M-198 | metalaxyl | propiconazole |
| M-199 | metalaxyl | prothioconazole |
| M-200 | metalaxyl | tebuconazole |
| M-201 | metalaxyl | triadimenol |
| M-202 | metalaxyl | triticonazole |
| M-203 | metalaxyl | imazalil |
| M-204 | metalaxyl | prochloraz |
| M-205 | metalaxyl | carbendazim |
| M-206 | metalaxyl | thiabendazole |
| M-207 | metalaxyl | ethaboxam |
| M-208 | metalaxyl | hymexazole |
| M-209 | metalaxyl | pyrimethanil |
| M-210 | metalaxyl | fludioxonil |
| M-211 | metalaxyl | aldimorph |
| M-212 | metalaxyl | dodemorph |
| M-213 | metalaxyl | fenpropimorph |
| M-214 | metalaxyl | iprodione |
| M-215 | metalaxyl | captan |
| M-216 | metalaxyl | fenoxanil |
| M-217 | metalaxyl | probenazol |
| M-218 | metalaxyl | mancozeb |
| M-219 | metalaxyl | metiram |
| M-220 | metalaxyl | thiram |
| M-221 | metalaxyl | ziram |
| M-222 | metalaxyl | guazatin |
| M-223 | metalaxyl | thiophanate-methyl |
| M-224 | metalaxyl | chlorothalonil |
| M-225 | metalaxyl | metrafenone |
| M-226 | cyproconazole | — |
| M-227 | cyproconazole | epoxiconazole |
| M-228 | cyproconazole | fenbuconazole |
| M-229 | cyproconazole | fluquinconazole |
| M-230 | cyproconazole | flutriafol |
| M-231 | cyproconazole | ipconazole |
| M-232 | cyproconazole | metconazole |
| M-233 | cyproconazole | propiconazole |
| M-234 | cyproconazole | prothioconazole |
| M-235 | cyproconazole | tebuconazole |
| M-236 | cyproconazole | triadimenol |
| M-237 | cyproconazole | triticonazole |
| M-238 | cyproconazole | imazalil |
| M-239 | cyproconazole | prochloraz |
| M-240 | cyproconazole | carbendazim |
| M-241 | cyproconazole | thiabendazole |
| M-242 | cyproconazole | ethaboxam |
| M-243 | cyproconazole | hymexazole |
| M-244 | cyproconazole | pyrimethanil |
| M-245 | cyproconazole | fludioxonil |
| M-246 | cyproconazole | aldimorph |
| M-247 | cyproconazole | dodemorph |
| M-248 | cyproconazole | fenpropimorph |
| M-249 | cyproconazole | iprodione |
| M-250 | cyproconazole | captan |
| M-251 | cyproconazole | fenoxanil |
| M-252 | cyproconazole | probenazol |
| M-253 | cyproconazole | mancozeb |
| M-254 | cyproconazole | metiram |
| M-255 | cyproconazole | thiram |
| M-256 | cyproconazole | ziram |
| M-257 | cyproconazole | guazatin |
| M-258 | cyproconazole | thiophanate-methyl |
| M-259 | cyproconazole | chlorothalonil |
| M-260 | cyproconazole | metrafenone |
| M-261 | epoxiconazole | — |
| M-262 | epoxiconazole | fenbuconazole |
| M-263 | epoxiconazole | fluquinconazole |
| M-264 | epoxiconazole | flutriafol |
| M-265 | epoxiconazole | ipconazole |
| M-266 | epoxiconazole | metconazole |
| M-267 | epoxiconazole | propiconazole |
| M-268 | epoxiconazole | prothioconazole |
| M-269 | epoxiconazole | tebuconazole |
| M-270 | epoxiconazole | triadimenol |
| M-271 | epoxiconazole | triticonazole |
| M-272 | epoxiconazole | imazalil |
| M-273 | epoxiconazole | prochloraz |
| M-274 | epoxiconazole | carbendazim |
| M-275 | epoxiconazole | thiabendazole |
| M-276 | epoxiconazole | ethaboxam |
| M-277 | epoxiconazole | hymexazole |
| M-278 | epoxiconazole | pyrimethanil |
| M-279 | epoxiconazole | fludioxonil |
| M-280 | epoxiconazole | aldimorph |
| M-281 | epoxiconazole | dodemorph |
| M-282 | epoxiconazole | fenpropimorph |
| M-283 | epoxiconazole | iprodione |
| M-284 | epoxiconazole | captan |
| M-285 | epoxiconazole | fenoxanil |

TABLE Q-continued

| Mixture No. | Compound IIB1 | Compound IIB2 |
|---|---|---|
| M-286 | epoxiconazole | probenazol |
| M-287 | epoxiconazole | mancozeb |
| M-288 | epoxiconazole | metiram |
| M-289 | epoxiconazole | thiram |
| M-290 | epoxiconazole | ziram |
| M-291 | epoxiconazole | guazatin |
| M-292 | epoxiconazole | thiophanate-methyl |
| M-293 | epoxiconazole | chlorothalonil |
| M-294 | epoxiconazole | metrafenone |
| M-295 | fenbuconazole | — |
| M-296 | fenbuconazole | fluquinconazole |
| M-297 | fenbuconazole | flutriafol |
| M-298 | fenbuconazole | ipconazole |
| M-299 | fenbuconazole | metconazole |
| M-300 | fenbuconazole | propiconazole |
| M-301 | fenbuconazole | prothioconazole |
| M-302 | fenbuconazole | tebuconazole |
| M-303 | fenbuconazole | triadimenol |
| M-304 | fenbuconazole | triticonazole |
| M-305 | fenbuconazole | imazalil |
| M-306 | fenbuconazole | prochloraz |
| M-307 | fenbuconazole | carbendazim |
| M-308 | fenbuconazole | thiabendazole |
| M-309 | fenbuconazole | ethaboxam |
| M-310 | fenbuconazole | hymexazole |
| M-311 | fenbuconazole | pyrimethanil |
| M-312 | fenbuconazole | fludioxonil |
| M-313 | fenbuconazole | aldimorph |
| M-314 | fenbuconazole | dodemorph |
| M-315 | fenbuconazole | fenpropimorph |
| M-316 | fenbuconazole | iprodione |
| M-317 | fenbuconazole | captan |
| M-318 | fenbuconazole | fenoxanil |
| M-319 | fenbuconazole | probenazol |
| M-320 | fenbuconazole | mancozeb |
| M-321 | fenbuconazole | metiram |
| M-322 | fenbuconazole | thiram |
| M-323 | fenbuconazole | ziram |
| M-324 | fenbuconazole | guazatin |
| M-325 | fenbuconazole | thiophanate-methyl |
| M-326 | fenbuconazole | chlorothalonil |
| M-327 | fenbuconazole | metrafenone |
| M-328 | fluquinconazole | — |
| M-329 | fluquinconazole | flutriafol |
| M-330 | fluquinconazole | ipconazole |
| M-331 | fluquinconazole | metconazole |
| M-332 | fluquinconazole | propiconazole |
| M-333 | fluquinconazole | prothioconazole |
| M-334 | fluquinconazole | tebuconazole |
| M-335 | fluquinconazole | triadimenol |
| M-336 | fluquinconazole | triticonazole |
| M-337 | fluquinconazole | imazalil |
| M-338 | fluquinconazole | prochloraz |
| M-339 | fluquinconazole | carbendazim |
| M-340 | fluquinconazole | thiabendazole |
| M-341 | fluquinconazole | ethaboxam |
| M-342 | fluquinconazole | hymexazole |
| M-343 | fluquinconazole | pyrimethanil |
| M-344 | fluquinconazole | fludioxonil |
| M-345 | fluquinconazole | aldimorph |
| M-346 | fluquinconazole | dodemorph |
| M-347 | fluquinconazole | fenpropimorph |
| M-348 | fluquinconazole | iprodione |
| M-349 | fluquinconazole | captan |
| M-350 | fluquinconazole | fenoxanil |
| M-351 | fluquinconazole | probenazol |
| M-352 | fluquinconazole | mancozeb |
| M-353 | fluquinconazole | metiram |
| M-354 | fluquinconazole | thiram |
| M-355 | fluquinconazole | ziram |
| M-356 | fluquinconazole | guazatin |
| M-357 | fluquinconazole | thiophanate-methyl |
| M-358 | fluquinconazole | chlorothalonil |
| M-359 | fluquinconazole | metrafenone |
| M-360 | flutriafol | — |
| M-361 | flutriafol | ipconazole |
| M-362 | flutriafol | metconazole |
| M-363 | flutriafol | propiconazole |
| M-364 | flutriafol | prothioconazole |
| M-365 | flutriafol | tebuconazole |
| M-366 | flutriafol | triadimenol |
| M-367 | flutriafol | triticonazole |
| M-368 | flutriafol | imazalil |
| M-369 | flutriafol | prochloraz |
| M-370 | flutriafol | carbendazim |
| M-371 | flutriafol | thiabendazole |
| M-372 | flutriafol | ethaboxam |
| M-373 | flutriafol | hymexazole |
| M-374 | flutriafol | pyrimethanil |
| M-375 | flutriafol | fludioxonil |
| M-376 | flutriafol | aldimorph |
| M-377 | flutriafol | dodemorph |
| M-378 | flutriafol | fenpropimorph |
| M-379 | flutriafol | iprodione |
| M-380 | flutriafol | captan |
| M-381 | flutriafol | fenoxanil |
| M-382 | flutriafol | probenazol |
| M-383 | flutriafol | mancozeb |
| M-384 | flutriafol | metiram |
| M-385 | flutriafol | thiram |
| M-386 | flutriafol | ziram |
| M-387 | flutriafol | guazatin |
| M-388 | flutriafol | thiophanate-methyl |
| M-389 | flutriafol | chlorothalonil |
| M-390 | flutriafol | metrafenone |
| M-391 | ipconazole | — |
| M-392 | ipconazole | metconazole |
| M-393 | ipconazole | propiconazole |
| M-394 | ipconazole | prothioconazole |
| M-395 | ipconazole | tebuconazole |
| M-396 | ipconazole | triadimenol |
| M-397 | ipconazole | triticonazole |
| M-398 | ipconazole | imazalil |
| M-399 | ipconazole | prochloraz |
| M-400 | ipconazole | carbendazim |
| M-401 | ipconazole | thiabendazole |
| M-402 | ipconazole | ethaboxam |
| M-403 | ipconazole | hymexazole |
| M-404 | ipconazole | pyrimethanil |
| M-405 | ipconazole | fludioxonil |
| M-406 | ipconazole | aldimorph |
| M-407 | ipconazole | dodemorph |
| M-408 | ipconazole | fenpropimorph |
| M-409 | ipconazole | iprodione |
| M-410 | ipconazole | captan |
| M-411 | ipconazole | fenoxanil |
| M-412 | ipconazole | probenazol |
| M-413 | ipconazole | mancozeb |
| M-414 | ipconazole | metiram |
| M-415 | ipconazole | thiram |
| M-416 | ipconazole | ziram |
| M-417 | ipconazole | guazatin |
| M-418 | ipconazole | thiophanate-methyl |
| M-419 | ipconazole | chlorothalonil |
| M-420 | ipconazole | metrafenone |
| M-421 | metconazole | — |
| M-422 | metconazole | propiconazole |
| M-423 | metconazole | prothioconazole |
| M-424 | metconazole | tebuconazole |
| M-425 | metconazole | triadimenol |
| M-426 | metconazole | triticonazole |
| M-427 | metconazole | imazalil |
| M-428 | metconazole | prochloraz |
| M-429 | metconazole | carbendazim |
| M-430 | metconazole | thiabendazole |
| M-431 | metconazole | ethaboxam |
| M-432 | metconazole | hymexazole |
| M-433 | metconazole | pyrimethanil |
| M-434 | metconazole | fludioxonil |

TABLE Q-continued

| Mixture No. | Compound IIB1 | Compound IIB2 |
|---|---|---|
| M-435 | metconazole | aldimorph |
| M-436 | metconazole | dodemorph |
| M-437 | metconazole | fenpropimorph |
| M-438 | metconazole | iprodione |
| M-439 | metconazole | captan |
| M-440 | metconazole | fenoxanil |
| M-441 | metconazole | probenazol |
| M-442 | metconazole | mancozeb |
| M-443 | metconazole | metiram |
| M-444 | metconazole | thiram |
| M-445 | metconazole | ziram |
| M-446 | metconazole | guazatin |
| M-447 | metconazole | thiophanate-methyl |
| M-448 | metconazole | chlorothalonil |
| M-449 | metconazole | metrafenone |
| M-450 | propiconazole | — |
| M-451 | propiconazole | prothioconazole |
| M-452 | propiconazole | tebuconazole |
| M-453 | propiconazole | triadimenol |
| M-454 | propiconazole | triticonazole |
| M-455 | propiconazole | imazalil |
| M-456 | propiconazole | prochloraz |
| M-457 | propiconazole | carbendazim |
| M-458 | propiconazole | thiabendazole |
| M-459 | propiconazole | ethaboxam |
| M-460 | propiconazole | hymexazole |
| M-461 | propiconazole | pyrimethanil |
| M-462 | propiconazole | fludioxonil |
| M-463 | propiconazole | aldimorph |
| M-464 | propiconazole | dodemorph |
| M-465 | propiconazole | fenpropimorph |
| M-466 | propiconazole | iprodione |
| M-467 | propiconazole | captan |
| M-468 | propiconazole | fenoxanil |
| M-469 | propiconazole | probenazol |
| M-470 | propiconazole | mancozeb |
| M-471 | propiconazole | metiram |
| M-472 | propiconazole | thiram |
| M-473 | propiconazole | ziram |
| M-474 | propiconazole | guazatin |
| M-475 | propiconazole | thiophanate-methyl |
| M-476 | propiconazole | chlorothalonil |
| M-477 | propiconazole | metrafenone |
| M-478 | prothioconazole | — |
| M-479 | prothioconazole | tebuconazole |
| M-480 | prothioconazole | triadimenol |
| M-481 | prothioconazole | triticonazole |
| M-482 | prothioconazole | imazalil |
| M-483 | prothioconazole | prochloraz |
| M-484 | prothioconazole | carbendazim |
| M-485 | prothioconazole | thiabendazole |
| M-486 | prothioconazole | ethaboxam |
| M-487 | prothioconazole | hymexazole |
| M-488 | prothioconazole | pyrimethanil |
| M-489 | prothioconazole | fludioxonil |
| M-490 | prothioconazole | aldimorph |
| M-491 | prothioconazole | dodemorph |
| M-492 | prothioconazole | fenpropimorph |
| M-493 | prothioconazole | iprodione |
| M-494 | prothioconazole | captan |
| M-495 | prothioconazole | fenoxanil |
| M-496 | prothioconazole | probenazol |
| M-497 | prothioconazole | mancozeb |
| M-498 | prothioconazole | metiram |
| M-499 | prothioconazole | thiram |
| M-500 | prothioconazole | ziram |
| M-501 | prothioconazole | guazatin |
| M-502 | prothioconazole | thiophanate-methyl |
| M-503 | prothioconazole | chlorothalonil |
| M-504 | prothioconazole | metrafenone |
| M-505 | tebuconazole | — |
| M-506 | tebuconazole | triadimenol |
| M-507 | tebuconazole | triticonazole |
| M-508 | tebuconazole | imazalil |
| M-509 | tebuconazole | prochloraz |
| M-510 | tebuconazole | carbendazim |
| M-511 | tebuconazole | thiabendazole |
| M-512 | tebuconazole | ethaboxam |
| M-513 | tebuconazole | hymexazole |
| M-514 | tebuconazole | pyrimethanil |
| M-515 | tebuconazole | fludioxonil |
| M-516 | tebuconazole | aldimorph |
| M-517 | tebuconazole | dodemorph |
| M-518 | tebuconazole | fenpropimorph |
| M-519 | tebuconazole | iprodione |
| M-520 | tebuconazole | captan |
| M-521 | tebuconazole | fenoxanil |
| M-522 | tebuconazole | probenazol |
| M-523 | tebuconazole | mancozeb |
| M-524 | tebuconazole | metiram |
| M-525 | tebuconazole | thiram |
| M-526 | tebuconazole | ziram |
| M-527 | tebuconazole | guazatin |
| M-528 | tebuconazole | thiophanate-methyl |
| M-529 | tebuconazole | chlorothalonil |
| M-530 | tebuconazole | metrafenone |
| M-531 | triadimenol | — |
| M-532 | triadimenol | triticonazole |
| M-533 | triadimenol | imazalil |
| M-534 | triadimenol | prochloraz |
| M-535 | triadimenol | carbendazim |
| M-536 | triadimenol | thiabendazole |
| M-537 | triadimenol | ethaboxam |
| M-538 | triadimenol | hymexazole |
| M-539 | triadimenol | pyrimethanil |
| M-540 | triadimenol | fludioxonil |
| M-541 | triadimenol | aldimorph |
| M-542 | triadimenol | dodemorph |
| M-543 | triadimenol | fenpropimorph |
| M-544 | triadimenol | iprodione |
| M-545 | triadimenol | captan |
| M-546 | triadimenol | fenoxanil |
| M-547 | triadimenol | probenazol |
| M-548 | triadimenol | mancozeb |
| M-549 | triadimenol | metiram |
| M-550 | triadimenol | thiram |
| M-551 | triadimenol | ziram |
| M-552 | triadimenol | guazatin |
| M-553 | triadimenol | thiophanate-methyl |
| M-554 | triadimenol | chlorothalonil |
| M-555 | triadimenol | metrafenone |
| M-556 | triticonazole | — |
| M-557 | triticonazole | imazalil |
| M-558 | triticonazole | prochloraz |
| M-559 | triticonazole | carbendazim |
| M-560 | triticonazole | thiabendazole |
| M-561 | triticonazole | ethaboxam |
| M-562 | triticonazole | hymexazole |
| M-563 | triticonazole | pyrimethanil |
| M-564 | triticonazole | fludioxonil |
| M-565 | triticonazole | aldimorph |
| M-566 | triticonazole | dodemorph |
| M-567 | triticonazole | fenpropimorph |
| M-568 | triticonazole | iprodione |
| M-569 | triticonazole | captan |
| M-570 | triticonazole | fenoxanil |
| M-571 | triticonazole | probenazol |
| M-572 | triticonazole | mancozeb |
| M-573 | triticonazole | metiram |
| M-574 | triticonazole | thiram |
| M-575 | triticonazole | ziram |
| M-576 | triticonazole | guazatin |
| M-577 | triticonazole | thiophanate-methyl |
| M-578 | triticonazole | chlorothalonil |
| M-579 | triticonazole | metrafenone |
| M-580 | imazalil | — |
| M-581 | imazalil | prochloraz |
| M-582 | imazalil | carbendazim |

TABLE Q-continued

| Mixture No. | Compound IIB1 | Compound IIB2 |
| --- | --- | --- |
| M-583 | imazalil | thiabendazole |
| M-584 | imazalil | ethaboxam |
| M-585 | imazalil | hymexazole |
| M-586 | imazalil | pyrimethanil |
| M-587 | imazalil | fludioxonil |
| M-588 | imazalil | aldimorph |
| M-589 | imazalil | dodemorph |
| M-590 | imazalil | fenpropimorph |
| M-591 | imazalil | iprodione |
| M-592 | imazalil | captan |
| M-593 | imazalil | fenoxanil |
| M-594 | imazalil | probenazol |
| M-595 | imazalil | mancozeb |
| M-596 | imazalil | metiram |
| M-597 | imazalil | thiram |
| M-598 | imazalil | ziram |
| M-599 | imazalil | guazatin |
| M-600 | imazalil | thiophanate-methyl |
| M-601 | imazalil | chlorothalonil |
| M-602 | imazalil | metrafenone |
| M-603 | prochloraz | — |
| M-604 | prochloraz | carbendazim |
| M-605 | prochloraz | thiabendazole |
| M-606 | prochloraz | ethaboxam |
| M-607 | prochloraz | hymexazole |
| M-608 | prochloraz | pyrimethanil |
| M-609 | prochloraz | fludioxonil |
| M-610 | prochloraz | aldimorph |
| M-611 | prochloraz | dodemorph |
| M-612 | prochloraz | fenpropimorph |
| M-613 | prochloraz | iprodione |
| M-614 | prochloraz | captan |
| M-615 | prochloraz | fenoxanil |
| M-616 | prochloraz | probenazol |
| M-617 | prochloraz | mancozeb |
| M-618 | prochloraz | metiram |
| M-619 | prochloraz | thiram |
| M-620 | prochloraz | ziram |
| M-621 | prochloraz | guazatin |
| M-622 | prochloraz | thiophanate-methyl |
| M-623 | prochloraz | chlorothalonil |
| M-624 | prochloraz | metrafenone |
| M-625 | carbendazim | — |
| M-626 | carbendazim | thiabendazole |
| M-627 | carbendazim | ethaboxam |
| M-628 | carbendazim | hymexazole |
| M-629 | carbendazim | pyrimethanil |
| M-630 | carbendazim | fludioxonil |
| M-631 | carbendazim | aldimorph |
| M-632 | carbendazim | dodemorph |
| M-633 | carbendazim | fenpropimorph |
| M-634 | carbendazim | iprodione |
| M-635 | carbendazim | captan |
| M-636 | carbendazim | fenoxanil |
| M-637 | carbendazim | probenazol |
| M-638 | carbendazim | mancozeb |
| M-639 | carbendazim | metiram |
| M-640 | carbendazim | thiram |
| M-641 | carbendazim | ziram |
| M-642 | carbendazim | guazatin |
| M-643 | carbendazim | thiophanate-methyl |
| M-644 | carbendazim | chlorothalonil |
| M-645 | carbendazim | metrafenone |
| M-646 | thiabendazole | — |
| M-647 | thiabendazole | ethaboxam |
| M-648 | thiabendazole | hymexazole |
| M-649 | thiabendazole | pyrimethanil |
| M-650 | thiabendazole | fludioxonil |
| M-651 | thiabendazole | aldimorph |
| M-652 | thiabendazole | dodemorph |
| M-653 | thiabendazole | fenpropimorph |
| M-654 | thiabendazole | iprodione |
| M-655 | thiabendazole | captan |
| M-656 | thiabendazole | fenoxanil |
| M-657 | thiabendazole | probenazol |
| M-658 | thiabendazole | mancozeb |
| M-659 | thiabendazole | metiram |
| M-660 | thiabendazole | thiram |
| M-661 | thiabendazole | ziram |
| M-662 | thiabendazole | guazatin |
| M-663 | thiabendazole | thiophanate-methyl |
| M-664 | thiabendazole | chlorothalonil |
| M-665 | thiabendazole | metrafenone |
| M-666 | ethaboxam | — |
| M-667 | ethaboxam | hymexazole |
| M-668 | ethaboxam | pyrimethanil |
| M-669 | ethaboxam | fludioxonil |
| M-670 | ethaboxam | aldimorph |
| M-671 | ethaboxam | dodemorph |
| M-672 | ethaboxam | fenpropimorph |
| M-673 | ethaboxam | iprodione |
| M-674 | ethaboxam | captan |
| M-675 | ethaboxam | fenoxanil |
| M-676 | ethaboxam | probenazol |
| M-677 | ethaboxam | mancozeb |
| M-678 | ethaboxam | metiram |
| M-679 | ethaboxam | thiram |
| M-680 | ethaboxam | ziram |
| M-681 | ethaboxam | guazatin |
| M-682 | ethaboxam | thiophanate-methyl |
| M-683 | ethaboxam | chlorothalonil |
| M-684 | ethaboxam | metrafenone |
| M-685 | hymexazole | — |
| M-686 | hymexazole | pyrimethanil |
| M-687 | hymexazole | fludioxonil |
| M-688 | hymexazole | aldimorph |
| M-689 | hymexazole | dodemorph |
| M-690 | hymexazole | fenpropimorph |
| M-691 | hymexazole | iprodione |
| M-692 | hymexazole | captan |
| M-693 | hymexazole | fenoxanil |
| M-694 | hymexazole | probenazol |
| M-695 | hymexazole | mancozeb |
| M-696 | hymexazole | metiram |
| M-697 | hymexazole | thiram |
| M-698 | hymexazole | ziram |
| M-699 | hymexazole | guazatin |
| M-700 | hymexazole | thiophanate-methyl |
| M-701 | hymexazole | chlorothalonil |
| M-702 | hymexazole | metrafenone |
| M-703 | pyrimethanil | — |
| M-704 | pyrimethanil | fludioxonil |
| M-705 | pyrimethanil | aldimorph |
| M-706 | pyrimethanil | dodemorph |
| M-707 | pyrimethanil | fenpropimorph |
| M-708 | pyrimethanil | iprodione |
| M-709 | pyrimethanil | captan |
| M-710 | pyrimethanil | fenoxanil |
| M-711 | pyrimethanil | probenazol |
| M-712 | pyrimethanil | mancozeb |
| M-713 | pyrimethanil | metiram |
| M-714 | pyrimethanil | thiram |
| M-715 | pyrimethanil | ziram |
| M-716 | pyrimethanil | guazatin |
| M-717 | pyrimethanil | thiophanate-methyl |
| M-718 | pyrimethanil | chlorothalonil |
| M-719 | pyrimethanil | metrafenone |
| M-720 | fludioxonil | — |
| M-721 | fludioxonil | aldimorph |
| M-722 | fludioxonil | dodemorph |
| M-723 | fludioxonil | fenpropimorph |
| M-724 | fludioxonil | iprodione |
| M-725 | fludioxonil | captan |
| M-726 | fludioxonil | fenoxanil |
| M-727 | fludioxonil | probenazol |
| M-728 | fludioxonil | mancozeb |
| M-729 | fludioxonil | metiram |

TABLE Q-continued

| Mixture No. | Compound IIB1 | Compound IIB2 |
|---|---|---|
| M-730 | fludioxonil | thiram |
| M-731 | fludioxonil | ziram |
| M-732 | fludioxonil | guazatin |
| M-733 | fludioxonil | thiophanate-methyl |
| M-734 | fludioxonil | chlorothalonil |
| M-735 | fludioxonil | metrafenone |
| M-736 | aldimorph | — |
| M-737 | aldimorph | dodemorph |
| M-738 | aldimorph | fenpropimorph |
| M-739 | aldimorph | iprodione |
| M-740 | aldimorph | captan |
| M-741 | aldimorph | fenoxanil |
| M-742 | aldimorph | probenazol |
| M-743 | aldimorph | mancozeb |
| M-744 | aldimorph | metiram |
| M-745 | aldimorph | thiram |
| M-746 | aldimorph | ziram |
| M-747 | aldimorph | guazatin |
| M-748 | aldimorph | thiophanate-methyl |
| M-749 | aldimorph | chlorothalonil |
| M-750 | aldimorph | metrafenone |
| M-751 | dodemorph | — |
| M-752 | dodemorph | fenpropimorph |
| M-753 | dodemorph | iprodione |
| M-754 | dodemorph | captan |
| M-755 | dodemorph | fenoxanil |
| M-756 | dodemorph | probenazol |
| M-757 | dodemorph | mancozeb |
| M-758 | dodemorph | metiram |
| M-759 | dodemorph | thiram |
| M-760 | dodemorph | ziram |
| M-761 | dodemorph | guazatin |
| M-762 | dodemorph | thiophanate-methyl |
| M-763 | dodemorph | chlorothalonil |
| M-764 | dodemorph | metrafenone |
| M-765 | fenpropimorph | — |
| M-766 | fenpropimorph | iprodione |
| M-767 | fenpropimorph | captan |
| M-768 | fenpropimorph | fenoxanil |
| M-769 | fenpropimorph | probenazol |
| M-770 | fenpropimorph | mancozeb |
| M-771 | fenpropimorph | metiram |
| M-772 | fenpropimorph | thiram |
| M-773 | fenpropimorph | ziram |
| M-774 | fenpropimorph | guazatin |
| M-775 | fenpropimorph | thiophanate-methyl |
| M-776 | fenpropimorph | chlorothalonil |
| M-777 | fenpropimorph | metrafenone |
| M-778 | iprodione | — |
| M-779 | iprodione | captan |
| M-780 | iprodione | fenoxanil |
| M-781 | iprodione | probenazol |
| M-782 | iprodione | mancozeb |
| M-783 | iprodione | metiram |
| M-784 | iprodione | thiram |
| M-785 | iprodione | ziram |
| M-786 | iprodione | guazatin |
| M-787 | iprodione | thiophanate-methyl |
| M-788 | iprodione | chlorothalonil |
| M-789 | iprodione | metrafenone |
| M-790 | captan | — |
| M-791 | captan | fenoxanil |
| M-792 | captan | probenazol |
| M-793 | captan | mancozeb |
| M-794 | captan | metiram |
| M-795 | captan | thiram |
| M-796 | captan | ziram |
| M-797 | captan | guazatin |
| M-798 | captan | thiophanate-methyl |
| M-799 | captan | chlorothalonil |
| M-800 | captan | metrafenone |
| M-801 | fenoxanil | — |
| M-802 | fenoxanil | probenazol |
| M-803 | fenoxanil | mancozeb |
| M-804 | fenoxanil | metiram |
| M-805 | fenoxanil | thiram |
| M-806 | fenoxanil | ziram |
| M-807 | fenoxanil | guazatin |
| M-808 | fenoxanil | thiophanate-methyl |
| M-809 | fenoxanil | chlorothalonil |
| M-810 | fenoxanil | metrafenone |
| M-811 | probenazol | — |
| M-812 | probenazol | mancozeb |
| M-813 | probenazol | metiram |
| M-814 | probenazol | thiram |
| M-815 | probenazol | ziram |
| M-816 | probenazol | guazatin |
| M-817 | probenazol | thiophanate-methyl |
| M-818 | probenazol | chlorothalonil |
| M-819 | probenazol | metrafenone |
| M-820 | mancozeb | — |
| M-821 | mancozeb | metiram |
| M-822 | mancozeb | thiram |
| M-823 | mancozeb | ziram |
| M-824 | mancozeb | guazatin |
| M-825 | mancozeb | thiophanate-methyl |
| M-826 | mancozeb | chlorothalonil |
| M-827 | mancozeb | metrafenone |
| M-828 | metiram | — |
| M-829 | metiram | thiram |
| M-830 | metiram | ziram |
| M-831 | metiram | guazatin |
| M-832 | metiram | thiophanate-methyl |
| M-833 | metiram | chlorothalonil |
| M-834 | metiram | metrafenone |
| M-835 | thiram | — |
| M-836 | thiram | ziram |
| M-837 | thiram | guazatin |
| M-838 | thiram | thiophanate-methyl |
| M-839 | thiram | chlorothalonil |
| M-840 | thiram | metrafenone |
| M-841 | ziram | — |
| M-842 | ziram | guazatin |
| M-843 | ziram | thiophanate-methyl |
| M-844 | ziram | chlorothalonil |
| M-845 | ziram | metrafenone |
| M-846 | guazatin | — |
| M-847 | guazatin | thiophanate-methyl |
| M-848 | guazatin | chlorothalonil |
| M-849 | guazatin | metrafenone |
| M-850 | thiophanate-methyl | — |
| M-851 | thiophanate-methyl | chlorothalonil |
| M-852 | thiophanate-methyl | metrafenone |
| M-853 | chlorothalonil | — |
| M-854 | chlorothalonil | metrafenone |
| M-855 | metrafenone | — |

The crystalline modification V and the one or more compound(s) of groups A.1-A.15 are usually applied in a weight ratio of from 500:1 to 1:100, preferably from 20:1 to 1:50, in particular from 5:1 to 1:20.

The afore-mentioned applies also to the ratios of combinations of modification V with fungicidal compounds IIA. Compounds IIB are usually combined with modification V in ratios from 100:1 to 1:100.

Depending on the desired effect, the application rates of the mixtures according to the invention are from 5 g/ha to 2000 g/ha, preferably from 50 to 1500 g/ha, in particular from 50 to 750 g/ha.

The crystalline modification V, the mixtures and the compositions according to the invention can be applied to any and all developmental stages, such as egg, larva, pupa, and adult. The pests may be controlled by contacting the target pest, its food supply, habitat, breeding ground or its locus with a pesticidally effective amount of the crystalline modification V, the mixtures or the compositions according to the invention.

"Locus" means a plant, seed, soil, area, material or environment in which a pest is growing or may grow.

In general, "pesticidally effective amount" means the amount of the crystalline modification V, the mixtures and the compositions according to the invention needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

The crystalline modification V, the mixtures and the compositions according to the invention can also be employed for protecting plants from attack or infestation by insects, acarids or nematodes comprising contacting a plant, or soil or water in which the plant is growing.

In the context of the present invention, the term plant refers to an entire plant, a part of the plant or the propagation material of the plant, that is, the seed or the seedling.

Plants which can be treated with the crystalline modification V, the mixtures and the compositions according to the invention include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

Some of the inventive mixtures and compositions have systemic action and can therefore be used for the protection of the plant shoot against foliar pests as well as for the treatment of the seed and roots against soil pests. The term seed treatment comprises all suitable seed treatment techniques known in the art, such as, but not limited to, seed dressing, seed coating, seed dusting, seed soaking, seed film coating, seed multilayer coating, seed encrusting, seed dripping, and seed pelleting.

The present invention also comprises seeds coated with or containing the crystalline modification V or the mixtures or the compositions according to the invention.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the crystalline modification V, the mixtures and the compositions according to the invention may also be used for the treatment seeds from plants, which tolerate the action of herbicides or fungicides or insecticides or nematicides owing to breeding, mutation and/or genetic engineering methods.

For example, the crystalline modification V, the mixtures and the compositions according to the invention can be employed in transgenic crops which are resistant to herbicides from the group consisting of the sulfonylureas (EP-A-0257993, U.S. Pat. No. 5,013,659), imidazolinones (see for example U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in plants resistant towards herbicides selected from the group of cyclohexadienone/aryloxyphenoxypropionic acid herbicides (U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in transgenic crop plants, for example cotton, with the capability of producing *Bacillus thuringiensis* toxins (Bt toxins) which make the plants resistant to certain pests (EP-A-0142924, EP-A-0193259).

Furthermore, the crystalline modification V, the mixtures and the compositions according to the invention can be used also for the treatment of seeds from plants, which have modified characteristics in comparison with existing plants consist, which can be generated, for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the crystalline modification V, the mixtures and the compositions according to the invention is carried out by spraying or dusting the seeds before sowing of the plants and before emergence of the plants.

In the treatment of seeds the corresponding formulations are applied by treating the seeds with an effective amount of the crystalline modification V, the mixtures or the compositions according to the invention. Herein, the application rates of the crystalline modification V are generally from 0.1 g to 10 kg per 100 kg of seed, preferably from 1 g to 5 kg per 100 kg of seed, in particular from 1 g to 2.5 kg per 100 kg of seed. For specific crops such as lettuce and onions the rates can be higher.

The mixtures and the compositions according to the invention are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non-crop pests such as ants, termites, wasps, flies, mosquitoes, crickets, locusts, or cockroaches the mixtures and the compositions according to the invention are prepared into a bait preparation.

The bait can be a liquid, a solid or a semisolid preparation (e.g. a gel). The bait employed in the mixtures/compositions is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a composition including the inventive mixtures, optionally a repellent and at least one binder.

The crystalline modification V, the mixtures and the compositions according to the invention can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient(s) is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the active ingredient(s) is from 0.001 to 80 weights %, preferably from 0.01 to 50 weight % and most preferably from 0.01 to 15 weight %.

For use in treating crop plants, the rate of application of the active ingredient(s) may be in the range of 0.1 g to 4000 g per hectare, desirably from 25 g to 600 g per hectare, more desirably from 50 g to 500 g per hectare.

It was also an object of the present invention to provide mixtures suitable for treating, controlling, preventing and protecting warm-blooded animals, including humans, and fish against infestation and infection by pests. Problems that may be encountered with pest control on or in animals and/or humans are similar to those described at the outset, namely the need for reduced dosage rates, and/or enhanced spectrum of activity and/or combination of knock-down activity with prolonged control and/or resistance management.

This invention also provides a method for treating, controlling, preventing and protecting warm-blooded animals, including humans, and fish against infestation and infection by pests of the orders Siphonaptera, Hymenoptera, Hemiptera, Orthoptera, Acarina, Phthiraptera, and Diptera, which comprises orally, topically or parenterally administering or applying to said animals a pesticidally effective amount of the crystalline modification V, the mixtures and the compositions according to the invention.

The invention also provides a process for the preparation of a composition for treating, controlling, preventing or protecting a warm-blooded animal or a fish against infestation or infection by pests of the Siphonaptera, Hymenoptera, Hemiptera, Orthoptera, Acarina, Phthiraptera, and Diptera orders which comprises a pesticidally effective amount of the crystalline modification V, the mixtures and the compositions according to the invention.

The above method is particularly useful for controlling and preventing infestations and infections in warm-blooded animals such as cattle, sheep, swine, camels, deer, horses, poultry, goats, dogs and cats as well as humans.

Infestations in warm-blooded animals and fish including, but not limited to, lice, biting lice, ticks, nasal bots, keds, biting flies, muscoid flies, flies, myiasitic fly larvae, chiggers, gnats, mosquitoes and fleas may be controlled, prevented or eliminated by the crystalline modification V, the mixtures and the compositions according to the invention.

For oral administration to warm-blooded animals, the crystalline modification V, the mixtures and the compositions according to the invention may be formulated as animal feeds, animal feed premixes, animal feed concentrates, pills, solutions, pastes, suspensions, drenches, gels, tablets, boluses and capsules. In addition, the crystalline modification V, the mixtures and the compositions according to the invention may be administered to the animals in their drinking water. For oral administration, the dosage form chosen should provide the animal with 0.01 mg/kg to 100 mg/kg of animal body weight per day of the crystalline modification V, the mixtures and the compositions according to the invention.

Alternatively, the crystalline modification V, the mixtures and the compositions according to the invention may be administered to animals parenterally, for example, by intraruminal, intramuscular, intravenous or subcutaneous injection. The crystalline modification V, the mixtures and the compositions according to the invention may be dispersed or dissolved in a physiologically acceptable carrier for subcutaneous injection. Alternatively, the crystalline modification V, the mixtures and the compositions according to the invention may be formulated into an implant for subcutaneous administration. In addition, the crystalline modification V, the mixtures and the compositions according to the invention may be transdermally administered to animals. For parenteral administration, the dosage form chosen should provide the animal with 0.01 mg/kg to 100 mg/kg of animal body weight per day of the crystalline modification V, the mixtures and the compositions according to the invention.

The crystalline modification V, the mixtures and the compositions according to the invention may also be applied topically to the animals in the form of dips, dusts, powders, collars, medallions, sprays, spot-on and pour-on formulations. For topical application, dips and sprays usually contain 0.5 ppm to 5000 ppm and preferably 1 ppm to 3000 ppm of the crystalline modification V. In addition, the crystalline modification V may be formulated as ear tags for animals, particularly quadrupeds such as cattle and sheep.

The figure and examples below serve to illustrate the invention and are not to be understood as limiting it.

FIG. 1: X-ray powder diffractogram of modification V

FIG. 2: Differential scanning calorimetry thermogram of modification V

FIG. 3: X-ray powder diffractograms of two mixtures of modifications I and V

PREPARATION EXAMPLES

All preparation procedures below were conducted with two samples of solid fipronil as starting materials which were obtained according to procedures as described in WO 01/30760, with final crystallization of the product from a solvent mixture of monochlorobenzene/ethanole (% by weight of ethanol at crystallization start: 13%) at temperatures of 70° C. to 35° C. This solid form in X-ray powder diffractogram studies proved to be crystalline fipronil of a mixture of several crystalline modifications. This mixture has been characterized to consist of crystalline modification I and crystalline modifications V, as for the first time identified and described in a co-pending application. A least squares refinement with the Topas program with simulated X-ray powder diffractogram patterns from single crystal data of form I and form V shows that in these two example samples, the percentage of form I varies from 30% to 70%. X-ray powder diffractograms of the two samples are shown in FIG. 3.

Irrespective of the sample of solid fipronil used as starting material, the crystallization procedures given in the examples given below gave the same inventive modification V. The solvates modification II and F-ST are preferably not used for evaporation crystallisations.

Example 1: Preparation of modification V by crystallization from acetonitrile 1 g of crystalline fipronil having a chemical purity of about 96% by weight was dissolved in 25 g of acetonitrile at 75 to 81° C. under reflux. The solution was kept at this temperature while the solvent was slowly evaporated with a gentle flow of inert $N_2$ gas. The solvent was left to evaporate for 3 days, after which the sample was cooled to 20° C. to 25° C. and the obtained dry crystalline material was filtered from some residual solvent on a paper filter by using vacuum. Crystallization yield>95%, melting point: 202° C. The material obtained has the X-ray powder diffractogram shown in FIG. 1 with the reflexes listed in Table 2 below.

Example 3: Preparation of modification V by crystallization from dimethylsulfoxide 0.5 g of crystalline fipronil having a chemical purity of about 96% by weight was dissolved in 10 ml of DMSO at 138 to 142° C. in a round bottomed flask. The solution was kept at this temperature while the solvent was slowly evaporated with a gentle flow of inert $N_2$ gas. The solvent was left to evaporate for about 15 hours, after which the sample was cooled to 20° C. to 25° C. and the obtained crystalline material was filtered from some residual solvent on a paper filter by using vacuum. Crystallization yield>85%, melting point: 202.5° C. The material obtained has the X-ray powder diffractogram shown in FIG. 1 with the reflexes listed in Table 2 below.

TABLE 2

| 2θ- and d-values of modification V | |
|---|---|
| 2θ (°) | d (Å) |
| 10.3 ± 0.2 | 8.55 ± 0.1 |
| 11.1 ± 0.2 | 7.94 ± 0.07 |
| 13.1 ± 0.2 | 6.78 ± 0.05 |
| 16.3 ± 0.2 | 5.43 ± 0.05 |
| 20.4 ± 0.2 | 4.35 ± 0.05 |
| 31.6 ± 0.2 | 2.83 ± 0.03 |

Analysis:

The picture of the X-ray powder diffractogram displayed in FIG. 1 was taken using a Siemens D-5000 diffractometer (manufacturer: Bruker AXS) in reflection geometry in the range from 2θ=2°–60° with increments of 0.02° using Cu—Kα radiation at 25° C.

The single crystal X-ray diffraction data was collected on a Bruker AXS CCD Detector using graphite $Cu_{K\alpha}$ radiation. The structure was solved by using direct methods, refined, and expanded by using Fourier techniques with the SHELX software package (G. M. Sheldrick, SHELX-97, Universität Göttingen, 1997). Absorption correction was performed with SADABS software The 2θ values found were used to calculate the stated interplanar spacing d. In FIG. 1. the intensity of the peaks (y-axis: linear intensity in counts) is plotted versus the 2θ angle (x-axis in degrees 2θ).

Heats of fusion indicated here refer to values determined by Differential scanning calorimetry (DSC) on a Mettler DSC 823 in air atmosphere with a heating rate of 5 K/min in the range from +30° to +230° C.

Melting points indicated herein refer to values determined on a Mettler hot stage microscope and represent equilibrium melting points.

DSC was performed on a Mettler Toledo DSC 823 module in air atmosphere. Crystals taken from the mother liquor were blotted dry on filter paper and place in crimped but vented aluminum sample pans for the DCS experiment. The sample size in each case was 5 to 10 mg. The temperature range was typically 30° C. to 230° C. at a heating rate of 5 K/min.

The invention claimed is:

1. A process for preparing the crystalline modification V comprising:
   i) preparing a solution of a solid form of fipronil being different from the crystalline modification V in a solvent S selected from dimethylsulfoxide at a temperature of 100° C. to 150° C. or acetonitrile at a temperature of 60° C. to 81° C.;
   ii) effecting crystallization of fipronil from the hot solution; and
   iii) isolating the resulting precipitate;
   wherein said crystalline modification shows, in an X-ray powder diffractogram recorded using Cu—Kα radiation at 25° C., at least 3 of the following reflexes:

$$2\theta = 10.3 \pm 0.2° \quad (1)$$

$$2\theta = 11.1 \pm 0.2° \quad (2)$$

$$2\theta = 13.0 \pm 0.2° \quad (3)$$

$$2\theta = 16.2 \pm 0.2° \quad (4)$$

$$2\theta = 20.3 \pm 0.2° \quad (5)$$

$$2\theta = 31.5 \pm 0.2°. \quad (6)$$

2. The process according to claim 1, wherein the solvent S is dimethylsulfoxide at a temperature of 130° C. to 150° C. or acetonitrile at a temperature of 70° C. to 81° C.

3. The process according to claim 2, wherein the solvent S is acetonitrile.

4. The process according to claim 2, wherein the solvent S is dimethylsulfoxide.

5. The process according to claim 1, wherein, in step ii), the crystallization of fipronil is effected by concentration of the solution obtained in step i).

6. The process according to claim 1, wherein step ii) is carried out in the presence of seed crystals of the crystalline modification V.

* * * * *

UNITED STATES PATENT AND TRADEMARK OFFICE
CERTIFICATE OF CORRECTION

PATENT NO. : 8,188,136 B2  
APPLICATION NO. : 12/513915  
DATED : May 29, 2012  
INVENTOR(S) : Heidi Emilia Saxell et al.

Page 1 of 1

It is certified that error appears in the above-identified patent and that said Letters Patent is hereby corrected as shown below:

In claim 1, col. 42, line 28, before "solution" insert --hot--.

Signed and Sealed this  
Twenty-fifth Day of September, 2012

David J. Kappos  
*Director of the United States Patent and Trademark Office*